United States Patent [19]

Briggs et al.

[11] Patent Number: 5,630,987
[45] Date of Patent: May 20, 1997

[54] METHOD AND APPARATUS FOR THE MEASUREMENT OF POLLUTANTS IN LIQUIDS

[75] Inventors: Ronald Briggs, Knebworth; Kenneth T. V. Grattan, Ickenham; Zoheir Movaziz, London, all of England

[73] Assignee: British Technology Group Limited, London, England

[21] Appl. No.: 374,658

[22] PCT Filed: Jul. 23, 1993

[86] PCT No.: PCT/GB93/01555

§ 371 Date: Jan. 24, 1995

§ 102(e) Date: Jan. 24, 1995

[87] PCT Pub. No.: WO94/02836

PCT Pub. Date: Feb. 3, 1994

[30] Foreign Application Priority Data

Jul. 24, 1992 [GB] United Kingdom ............... 9215741

[51] Int. Cl.[6] .................................................. G01N 21/59
[52] U.S. Cl. .......................... 422/82; 422/82.09; 436/53; 436/178
[58] Field of Search ............................ 422/81, 82, 82.05, 422/82.09, 91, 93; 436/52, 53, 177, 178, 164, 171

[56] References Cited

U.S. PATENT DOCUMENTS

| | | | |
|---|---|---|---|
| 3,840,341 | 10/1974 | Rogers | 436/146 |
| 3,977,836 | 8/1976 | Matsuda | 436/116 X |
| 4,111,560 | 9/1978 | Jolanki et al. | |
| 4,296,086 | 10/1981 | Whitehead | 436/116 X |
| 4,357,143 | 11/1982 | Scott | |
| 4,526,870 | 7/1985 | Muller | |
| 5,107,118 | 4/1992 | Murray et al. | |
| 5,312,756 | 5/1994 | Jolly | 436/178 X |

FOREIGN PATENT DOCUMENTS

| | | |
|---|---|---|
| 0310740 | 4/1989 | European Pat. Off. |
| 3303337 | 8/1984 | Germany |

OTHER PUBLICATIONS

Analytical Instrumentation, vol. 15, No. 4, Dec. 1 1986, pp. 287-308 Voigtman et al "Basis and Use of Lock-In Detection, ETS".

Measurement Techniques, vol. 24, No. 6, Jun. 1 1981, New York, pp. 515-518 Dolginov et al "Use of Light Emitting Diodes, Etc".

Primary Examiner—Jeffrey Snay
Attorney, Agent, or Firm—Cushman, Darby & Cushman

[57] ABSTRACT

An apparatus for measuring the concentration of a contaminant in a fluid includes a measuring chamber in a fluid path, a first source of optical radiation of a predetermined wavelength adapted to direct the radiation through the measuring chamber, and a detector for detecting the radiation after passage through the measuring chamber. The fluid path also has a pump provided to urge a test fluid from a fluid source to the measuring chamber, the test fluid being subjected to containing the contaminant, a fluid processor to process the fluid to change an optical effect of the contaminant, an acid wash to inhibit the effect of precipitation of cations within the fluid path, a fluid bypass to bypass the fluid processor and a valve to alternately direct the fluid to the fluid processor and the bypass.

8 Claims, 32 Drawing Sheets pump pulse
conditioner 1 to sample
& hold 1 pulse conditioner 1 to sample & hold 2 pump = bcde    a = main clock signal
pulse conditioner 1 = pump · f    b,c,d,e,f = outputs of counter

METHOD AND APPARATUS FOR THE MEASUREMENT OF POLLUTANTS IN LIQUIDS

FIELD OF THE INVENTION

This invention relates to an apparatus and a method used to measure concentration of chemical pollutants such as ammonia, nitrate ions, organic matter and suspended matter in fluids such as water.

BACKGROUND AND SUMMARY OF THE INVENTION

An instrument has been developed to use absorption of radiation for the on-line determination of the concentration of contaminants such as nitrate ions, ammonia and organic matter which are indicative of the extent of pollution occurring in a wide range of natural and processed waters.

UV spectroscopy can be utilized for the determination of most organic and certain non-organic compounds (e.g. chlorine) using simple techniques. This method relies on the absorption of light in a more restricted band than the visible i.e. from 180 to 400 nm. Many elements absorb ultra-violet light selectively in the band from 200 to 300 nm, each at a specific wavelength. The absorption peak profile is wide since it results from absorption from different origins, mainly due to electronic transitions on to which vibrations, rotations and translation are superimposed. As a consequence, characterization of the sensing wavelength is not very specific. It is not always possible to provide light of adequate intensity at the wavelength of peak absorption. Hence an adjacent wavelength must be used, even though it reduces the sensitivity somewhat. Another alternative which is more complex and costly would be the use of a grating system to provide any particular wavelength and deconvoluting the spectra obtained. However, in the simple system chosen, deviations from the peak absorption wavelength do not give rise to major difficulties.

According to the present invention there is provided an apparatus for measuring the level of a contaminant in a fluid comprising a measuring chamber, a first source of optical radiation of a predetermined wavelength adapted to direct the radiation through the chamber, detector means to detect the radiation after passage through the measuring chamber, pump means to urge a test fluid test from a fluid source to the measuring chamber, fluid processing means positioned between the fluid source and the measuring chamber to process the fluid to change an optical effect of the contaminant, bypass means to bypass the fluid processing means and valve means alternately to direct the fluid to the processing means and the bypass means.

BRIEF DESCRIPTION OF THE DRAWINGS

The invention will now be particularly described with reference to the accompanying drawings in which.

DESCRIPTION OF THE PREFERRED EMBODIMENT

The optical properties of nitrate ions, ammonia, suspended and organic matter were investigated in detail. As a result it was decided to use 253.7 nm as the wavelength for absorption of ammonia (measured as monochloramine), suspended and organic matter. Although monochloramine absorbs at 244 nm, the sensitivity of the measurement carried out at 253.7 nm was found to be acceptable since the peak of absorption is very broad for elements absorbing in the ultra-violet region.

The use of two different types of resins was found to be suitable for provision of background measurement on the samples. Hence it is practical to use the 253.7 nm wavelength as the measuring wavelength for ammonia, organic and suspended matter, making it possible to use a single light source and optical cell for measurement of these parameters. Nitrate ion, however, require a different light source and sample cell because the absorption peak was found to be at a wavelength of 200 nm.

Nitrate ion have a strong absorption peak at a band of wavelengths between 200 to 210 nm. Scans using a spectrophotometer show that on a sample of distilled water to which nitrate has been added, the maximum absorption for nitrate is situated at 200 nm.

A powder of sodium nitrate ($NaNO_3$) of 100% purity was mixed with distilled water to provide a stock of standard solution with a nitrate ion concentration of 2 g/l. This solution was used in all of the experiments.

Figure 1:
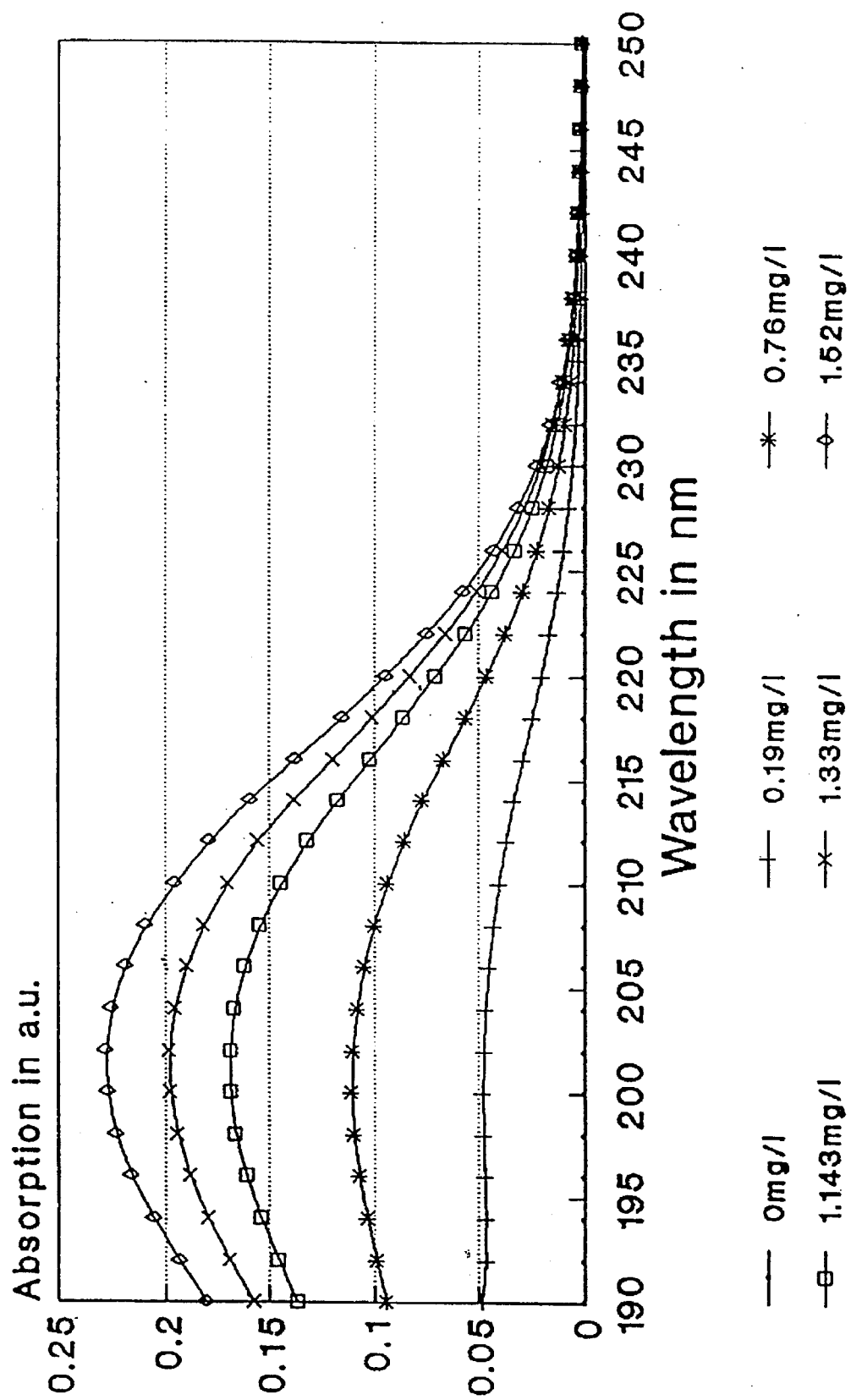
FIGS. 1 to 19 illustrate various optical effects.
Figure 2:
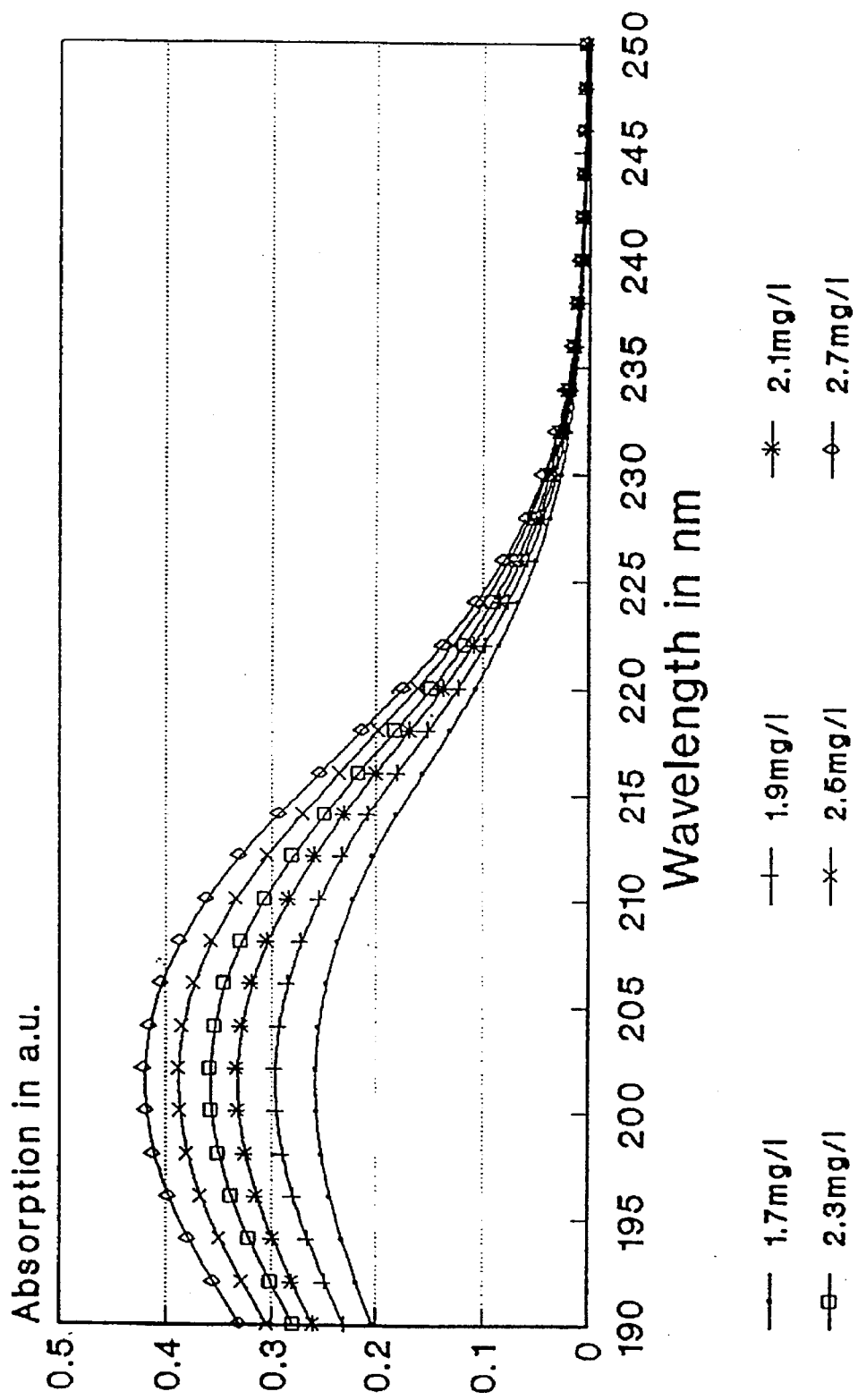
Figure 3:
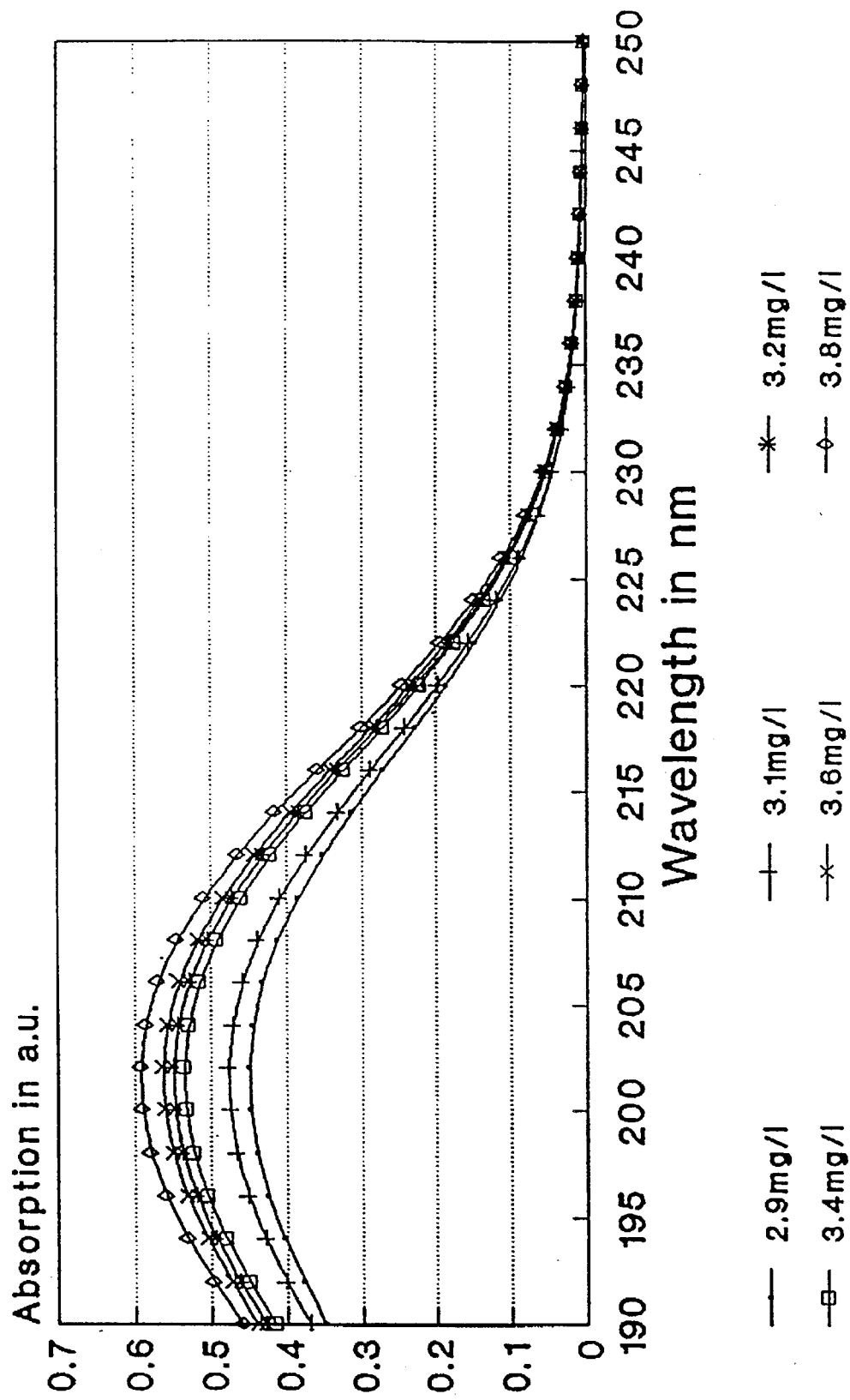
Figure 4:
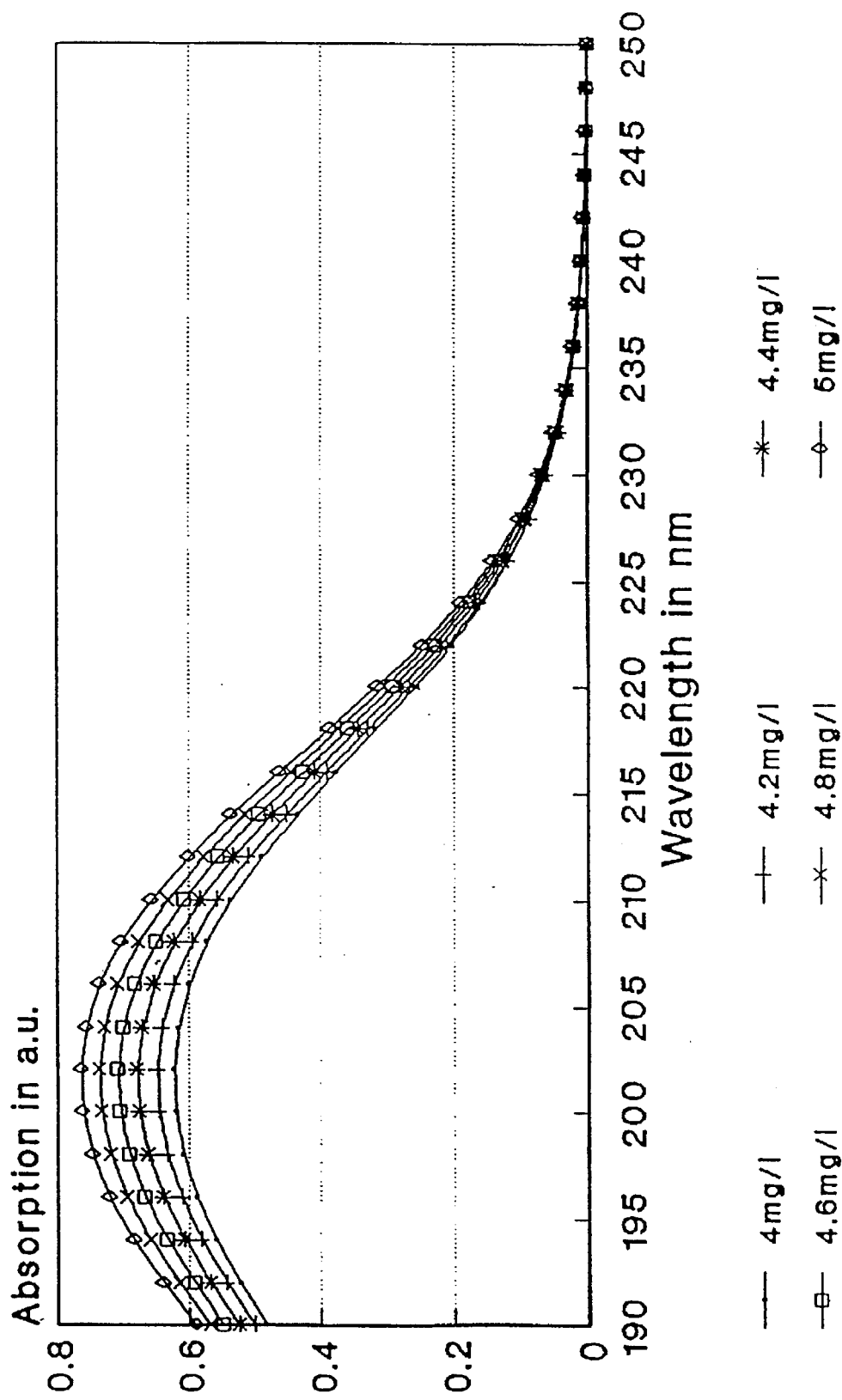
Figure 5:
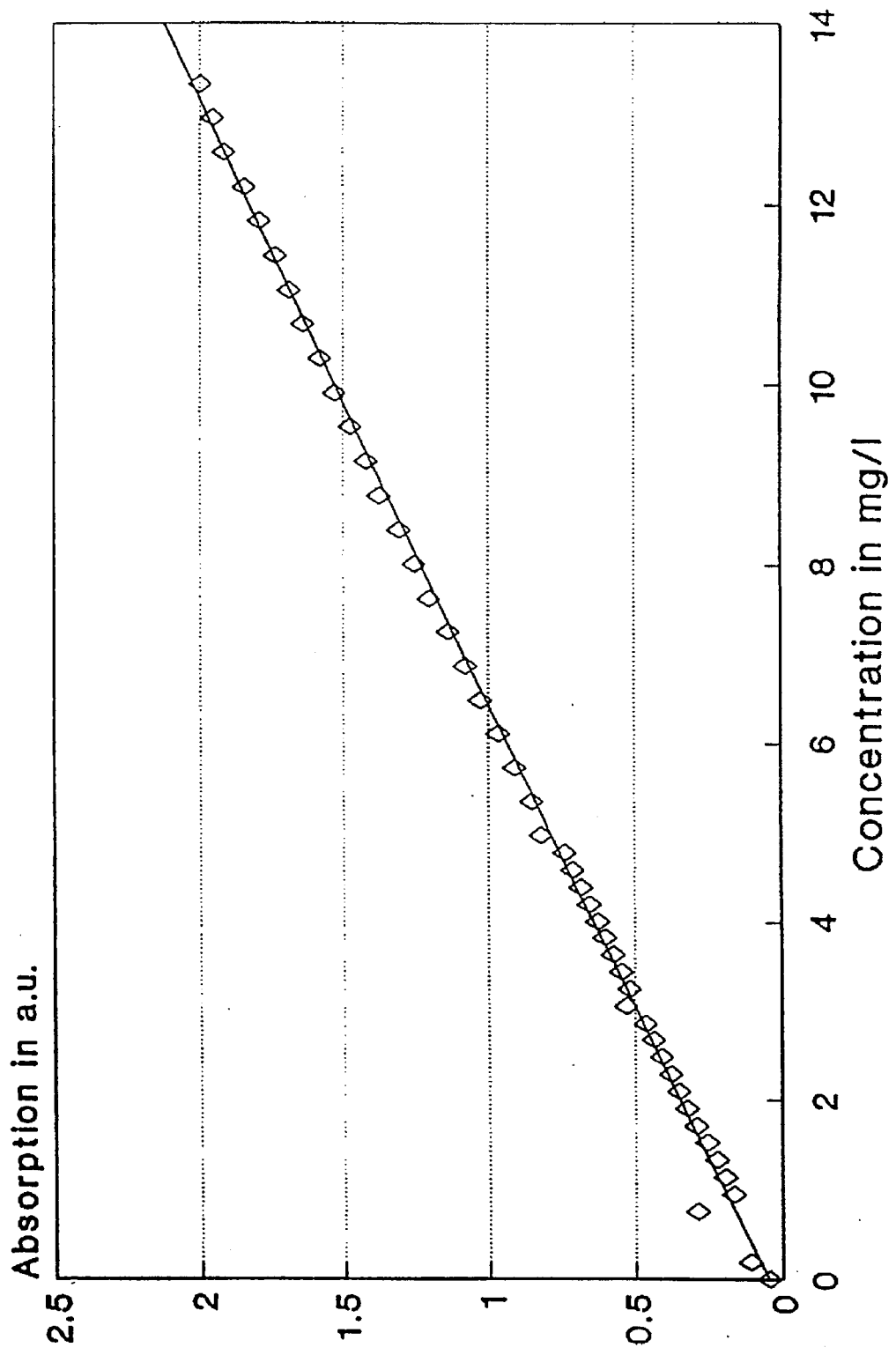
Figure 6:
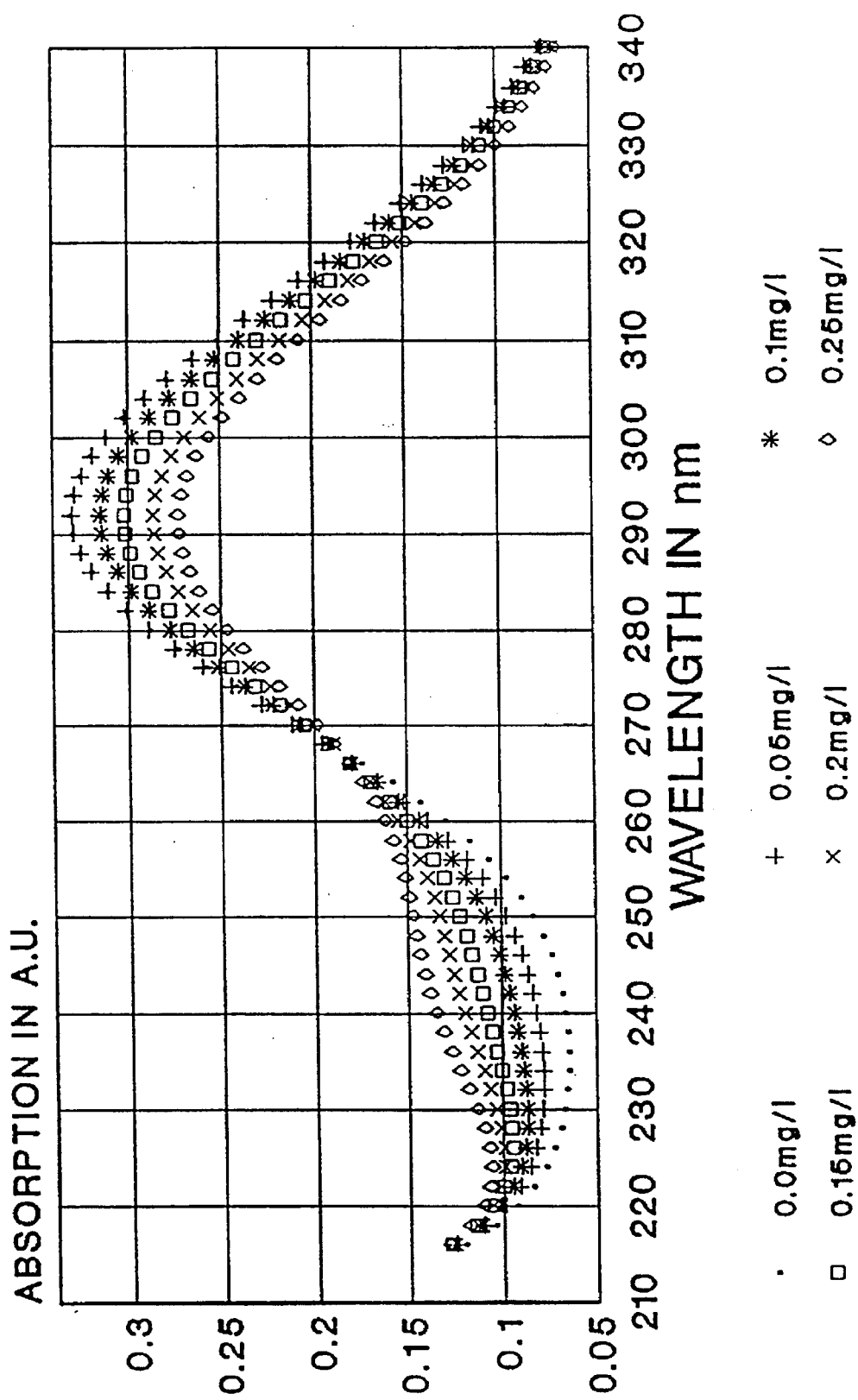
Figure 7:
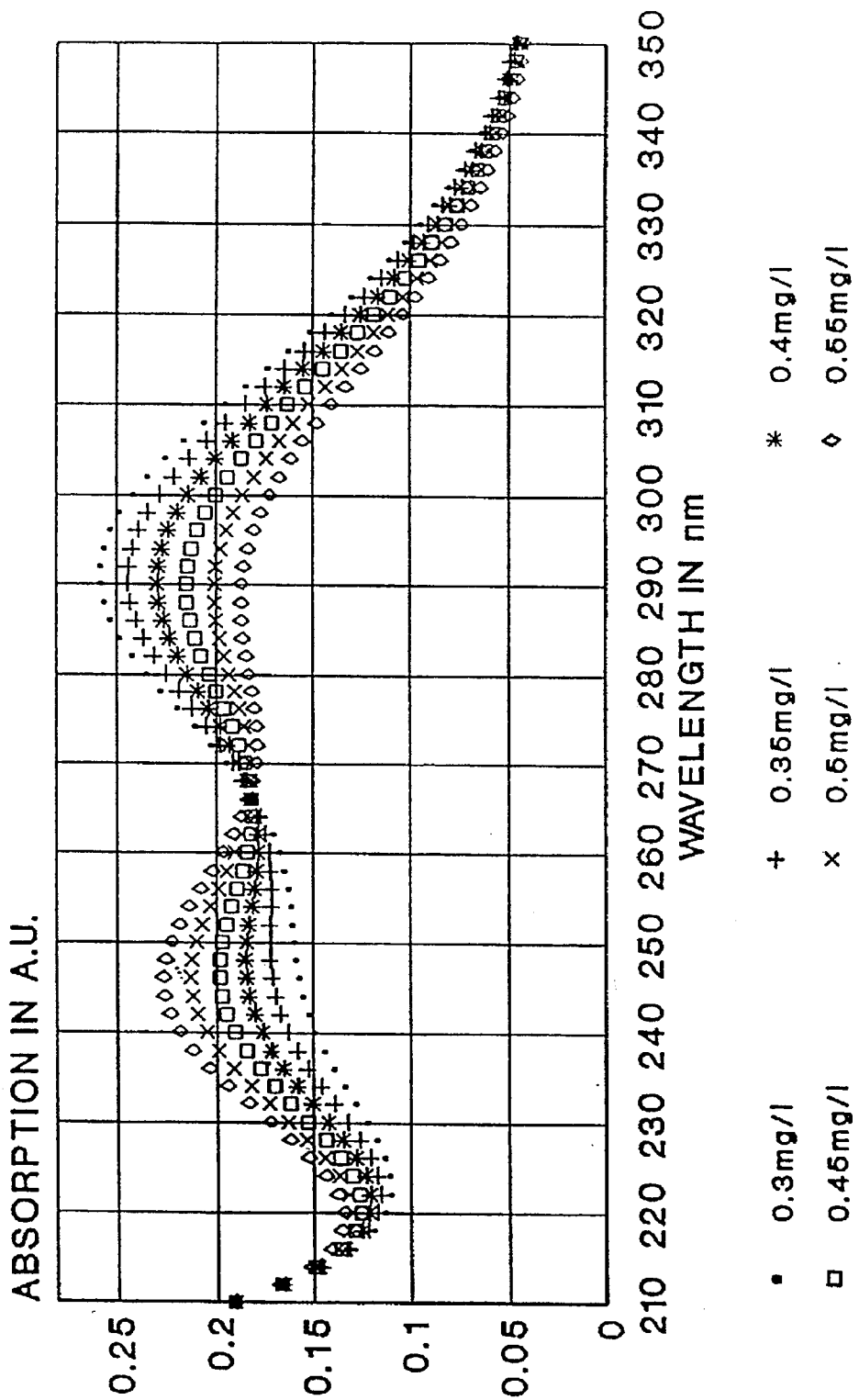
Figure 8:
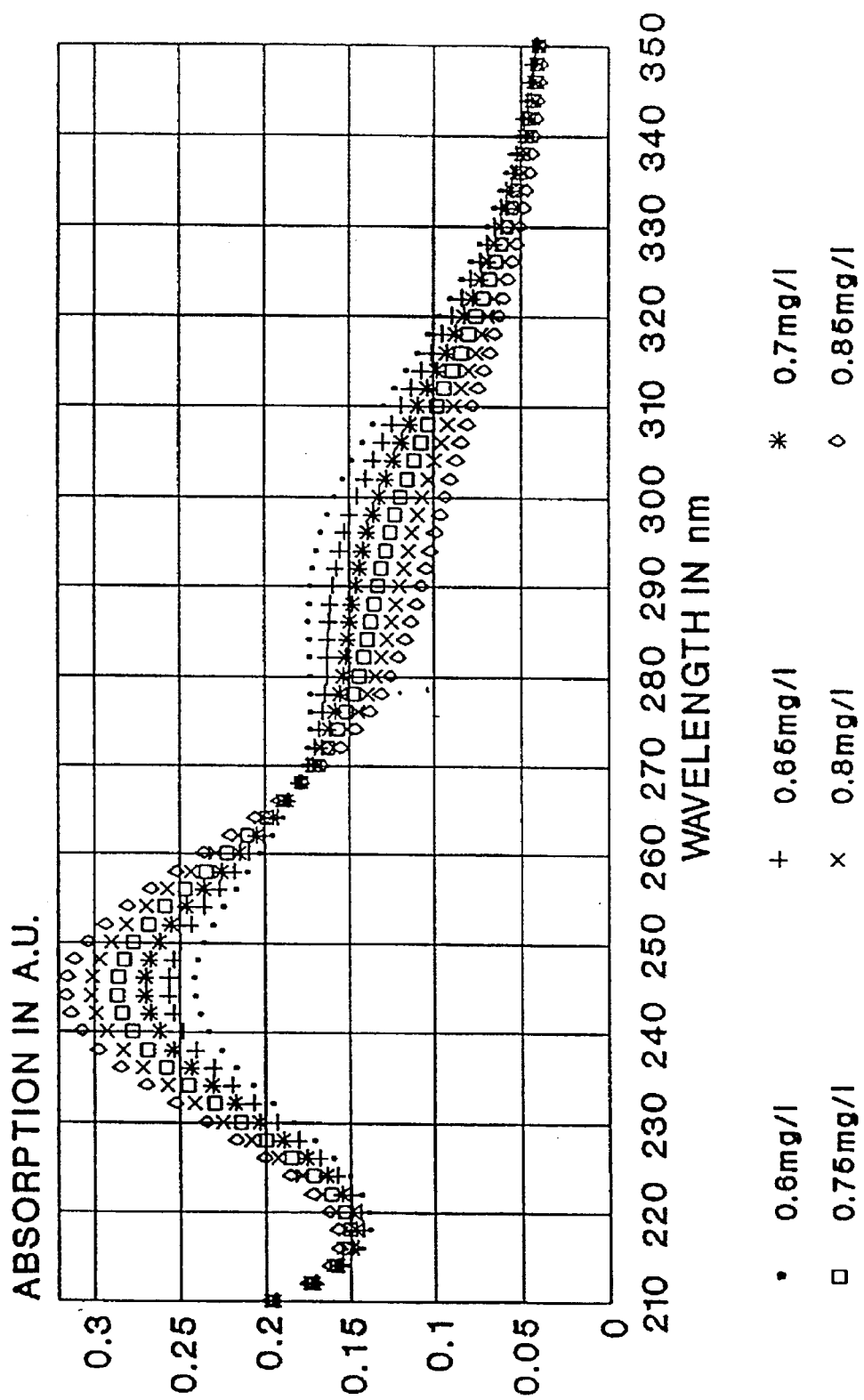
Figure 9:
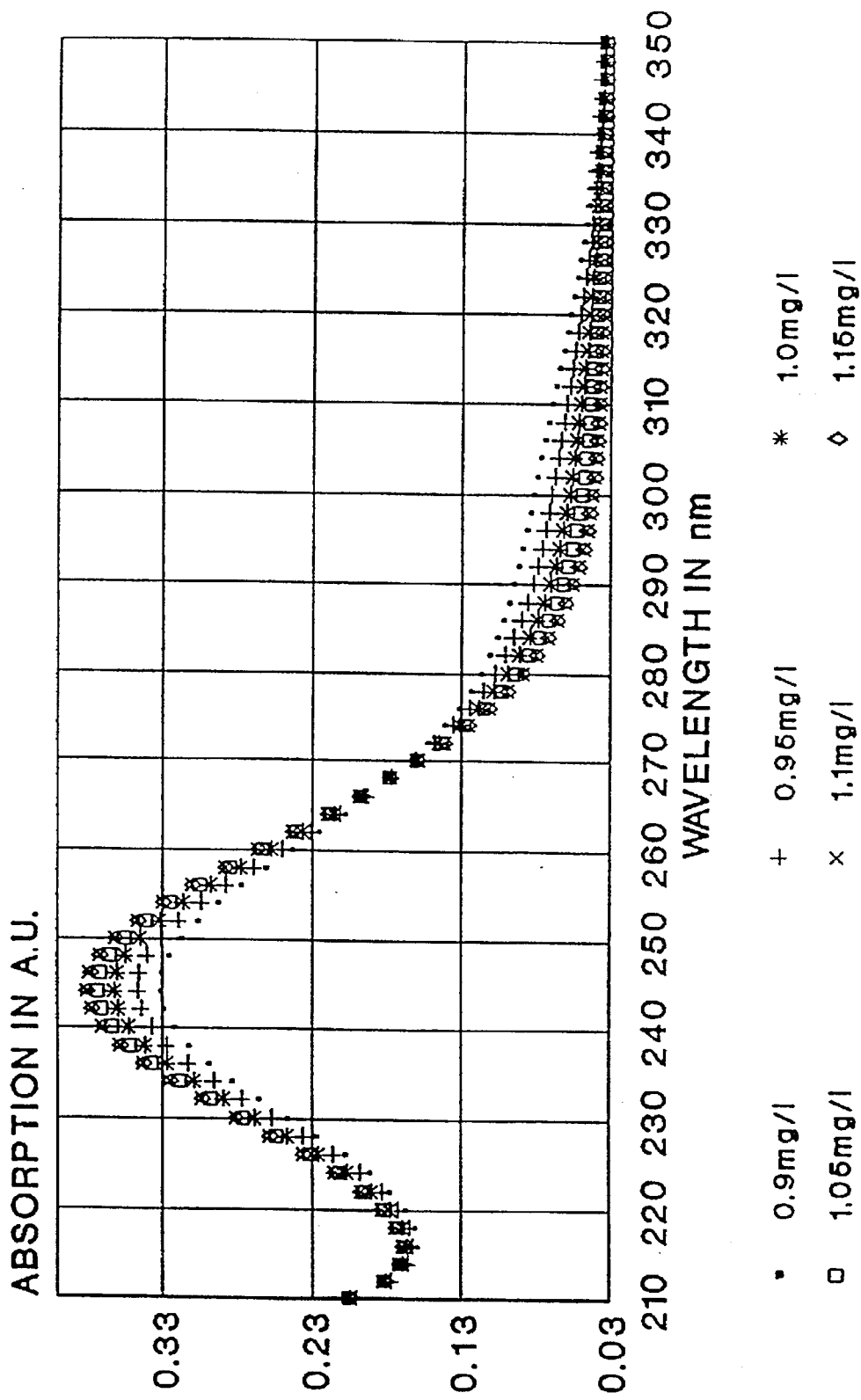

FIGS. 1, 2, 3 and 4 represent the absorption spectra of different concentrations of nitrate ion in solution in the region of 190 to 250 nm. The range of concentration deployed was 0 to 13 mg/l. The latter being the highest concentration level since the maximum limit of absorption of the spectrophotometer was reached. For higher concentrations, the sample may be diluted or the path length reduced, the original path length being 10 mm. A plot of the optical density versus nitrate ion concentration is shown in FIG. 5.

For the range of concentration studied it was found that the relation between absorption and concentration was linear and could be expressed as follows:

$$Y = aC + b$$

where a represents the slope of the line and b the background absorption (i.e. for C=0), C is the nitrate ion concentration expressed in mg/l. It was also found that the slope of the curve represented by a is 0.15 a/mg/l and b=0.

Nitrate ion concentration can therefore be measured using optical techniques. A suitable operating wavelength is 200 nm but a light source made from a mixture of iodine and mercury which can generate a line emission at 206 nm was found to be suitable but the sensitivity of the measurement was reduced by 4%.

The sensitivity of the measurement is a function of the signal-to-noise ratio and the limit of detection is therefore dictated by the noise level in the detected signal. A signal-to-noise ratio of 40 dB has been reached using an optical cell with a pathlength of 10 mm.

The range of concentration of nitrate ions (0 to 13 mg/l) studied was measured. The background absorption was provided by measuring a sample that had been filtered with a resin that removed the nitrate ions from the sample and allows for the measurement of the absorption of any element other than nitrate ions and also for instrumental errors. The resin has a high removal capacity but nevertheless has to be regenerated after a specific time. This time is a function of the flow rate, the volume of resin used and the amount of nitrate ions present in the sample.

Ammonia absorbs in the ultraviolet region of the spectrum i.e. 180 nm but this peak is too close to the nitrate peak, hence it is affected by the level of nitrate in the sample. For this reason it cannot be utilized to determine the concentration of ammonia in the sample. Monochloramine, which is one of the products of the reaction of ammonia with chlorine absorbs at 244 nm. The reaction also produces dichloramine and trichloramine when an excess of chlorine is available. However, the reaction of monochloramine with chlorine is slow and the reaction of dichloramine with chlorine is even slower. Hence if the measurement is carried out in a relatively short time, monochloramine can be used for the measurement of ammonia. A second attraction of using monochloramine is that both di- and trichloramine do not absorb in the UV spectrum. Additionally suitable light sources and detectors are readily available.

Figure 11:
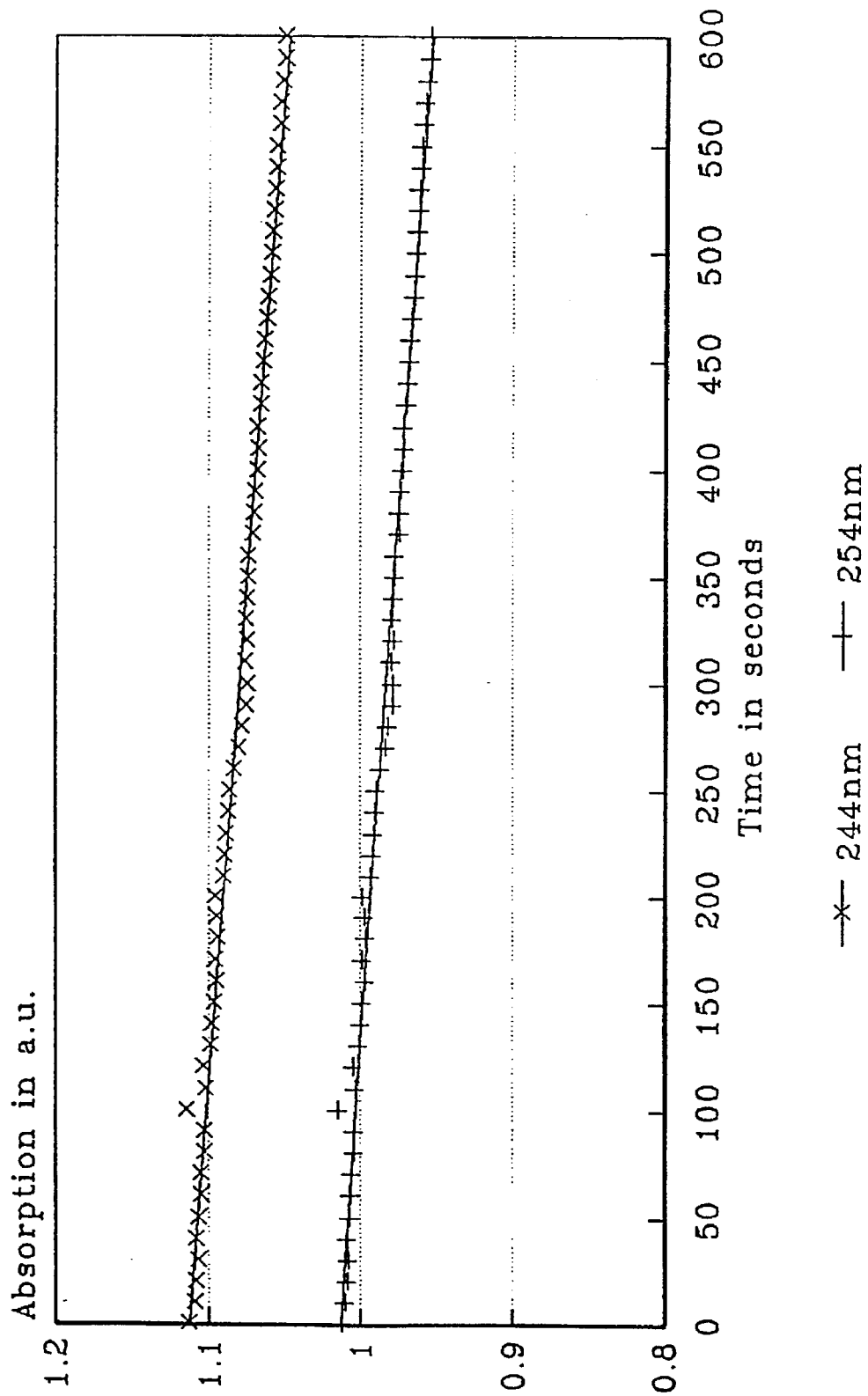

A spectral analysis of monochloramine is depicted in FIGS. 6, 7, 8 and 9 for a range of concentrations of 0 to 2 mg/l on a sample of distilled water. Different concentrations of ammonia have been added to a solution of distilled water to which a fixed concentration of chlorine (130 mg/l) was added prior to the addition of ammonia. The sample was scanned immediately after adding ammonia to minimize the effect of monochloramine reacting with the excess chlorine present. A test on the reaction time of monochloramine with chlorine was carried out in order to establish the time at which the measurement should be made and that very little of the monochloramine had been able to react with the excess chlorine. Samples were taken every ten seconds and the results of the test are shown in FIG. 11.

Although the peak of absorption is situated at 244 nm, the wavelength of 253.7 nm can be used for the purpose of measuring monochloramine concentration with very little loss of sensitivity. Measurements of monochloramine were made in steps of 100 μg/l.

Figure 10:
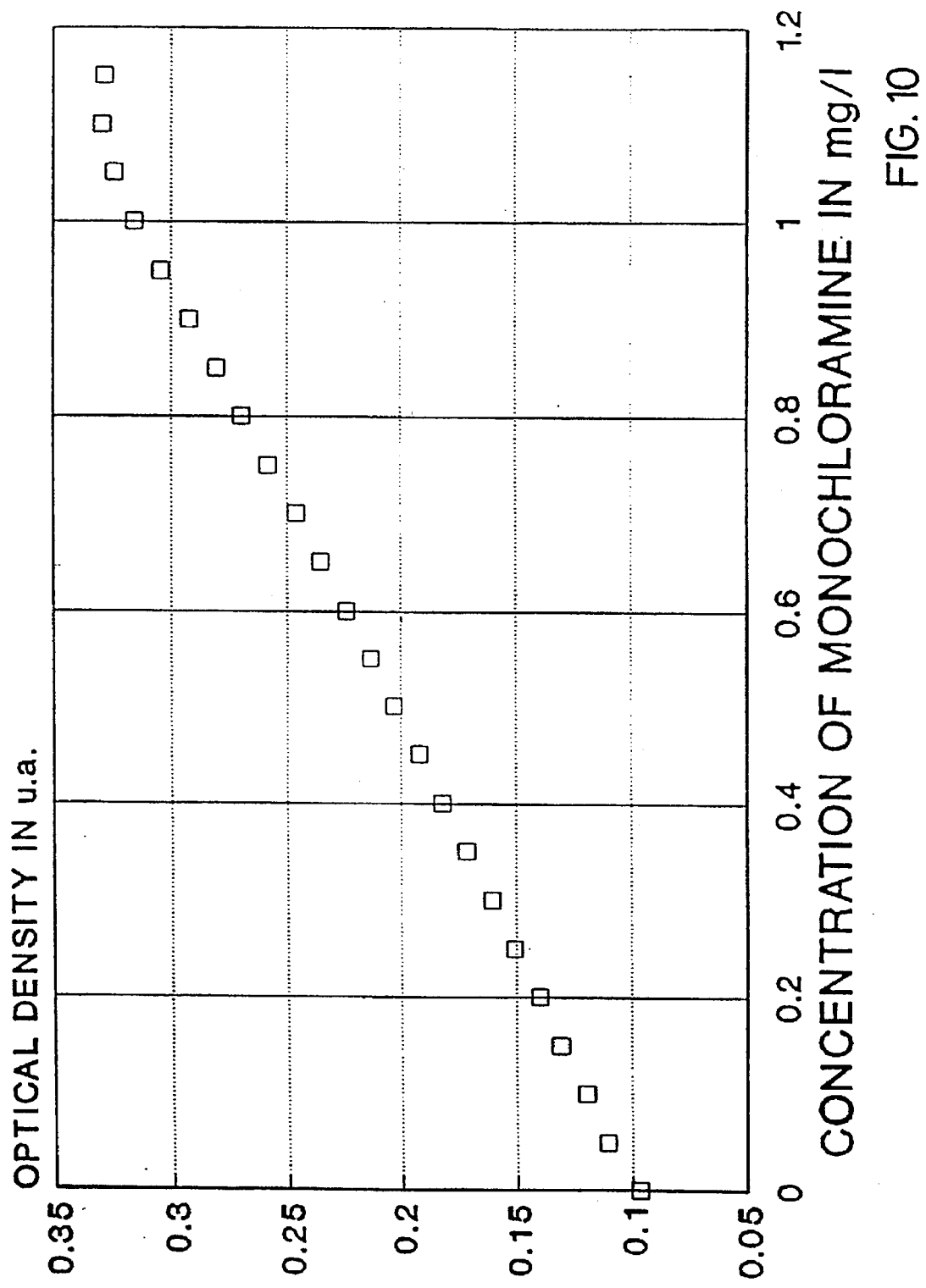

FIG. 10 represents the linear relationship found between light absorption and monochloramine concentration in the range 0 to 2 mg/l. This relationship can be expressed in mathematical terms for calibration purposes and is as follows:

$$Y = aC + b$$

$a = 0.22 a/mg/l$ and $b = 0.09$ a.u.
b represents the background absorption which in the case of distilled water is 0.09 absorption units (a.u.). This is not the case with different sources of water. The reference (background measurement) can be obtained by measuring the absorption of monochloramine at 253.7 nm prior to the addition of the chlorine. The decrease in sensitivity can be calculated from the difference in slopes of calibration and are found to be 25%.

Figure 12:
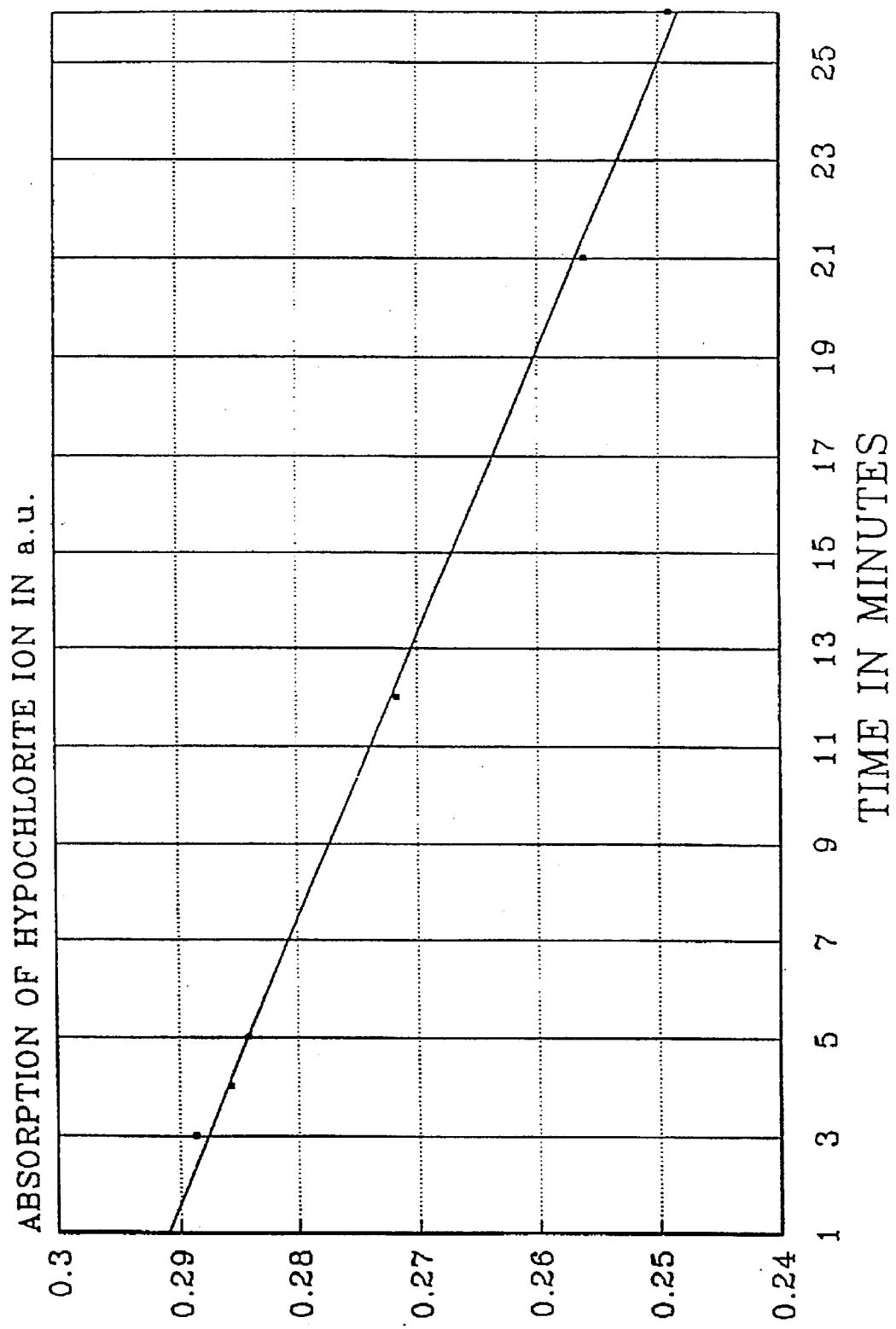
Figure 13:
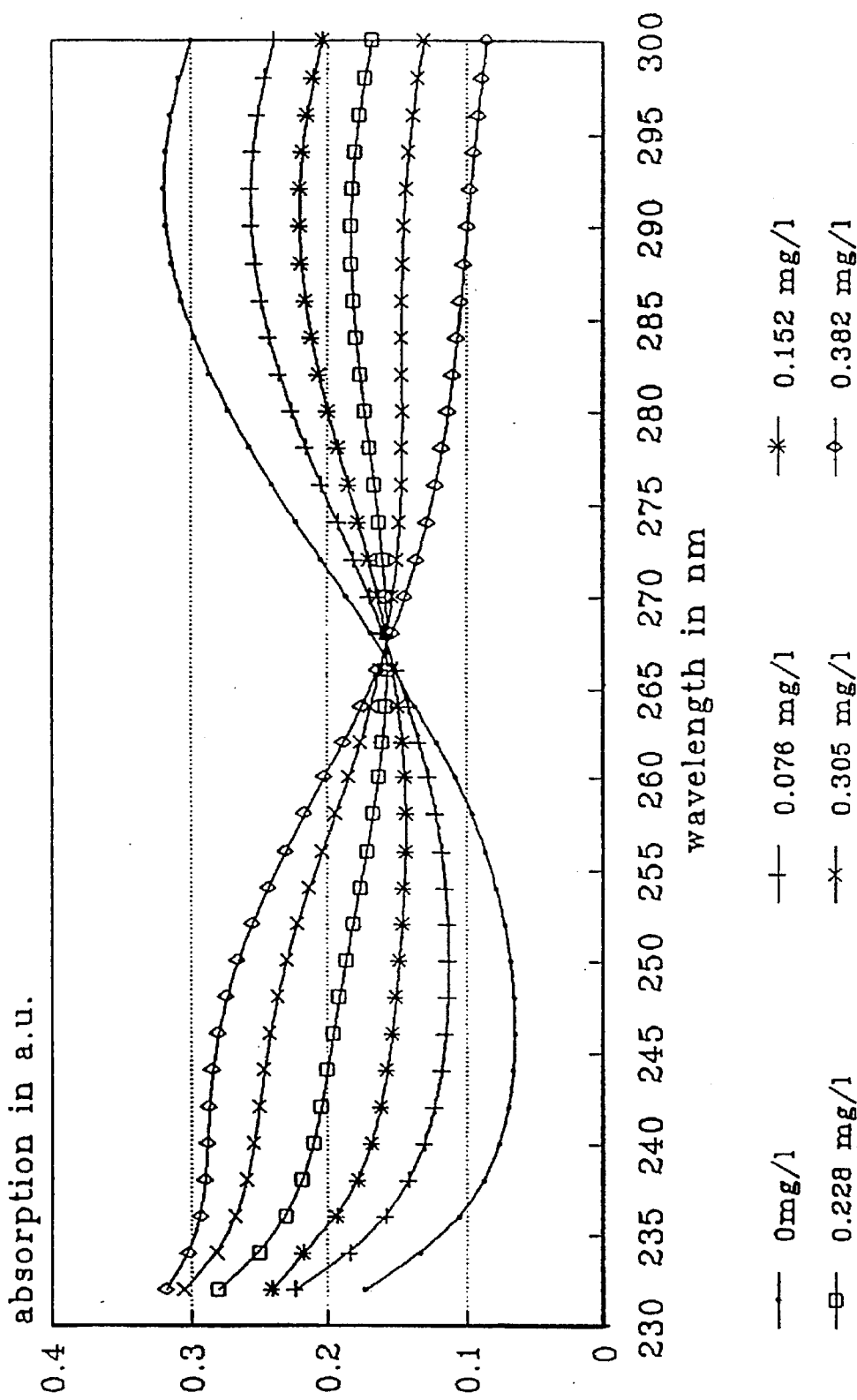

FIG. 11 represents the decrease of absorption of monochloramine with time in a sample of distilled water in the presence of excess chlorine. FIG. 12 shows the consumption of chlorine by monochloramine when it produced dichloramine after reacting with chlorine for the first 20 minutes. The rate of monochloramine consumption was measured as diminution in absorption level and was found to be $0.114 \times 10^{-3}$ a.u./second. However, this minimum time is not critical as long as it is kept constant. The error introduced in the measurement is minimum when the same calibration curve and timing are used.

Figure 14:
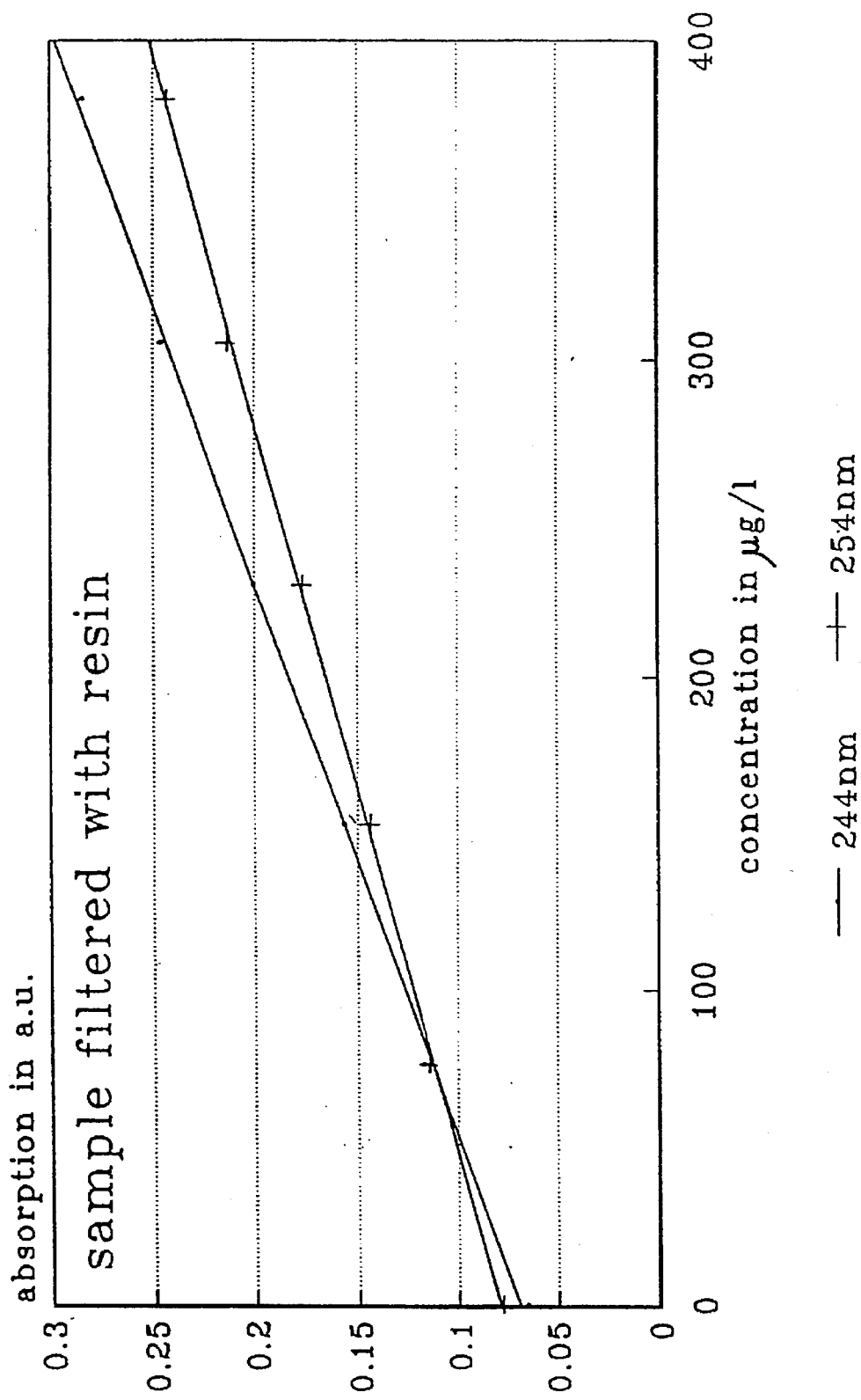

FIG. 14 represents the absorption spectra of monochloramine using 244 and 254 nm. The differences in slopes in FIG. 14 show the loss of sensitivity in the measurement and has been calculated to be 26%.

IMAC HP441 resin was found to be suitable for the removal of organic matter and HP555 resin was found to be suitable for nitrate removal. The efficiency of removal was tested on different types of water from distilled water to swimming pool and tap water.

Figure 15:
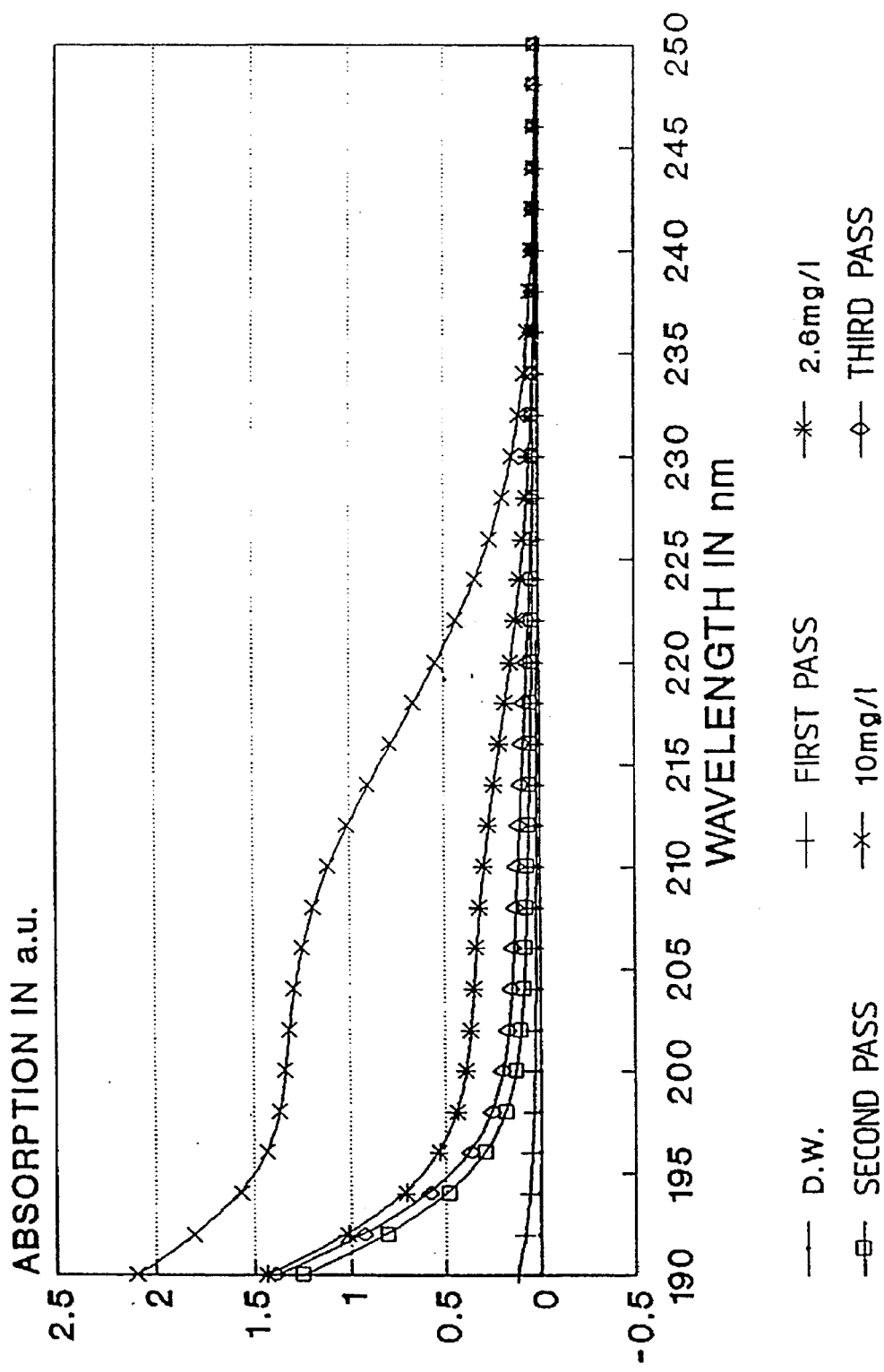
Figure 16:
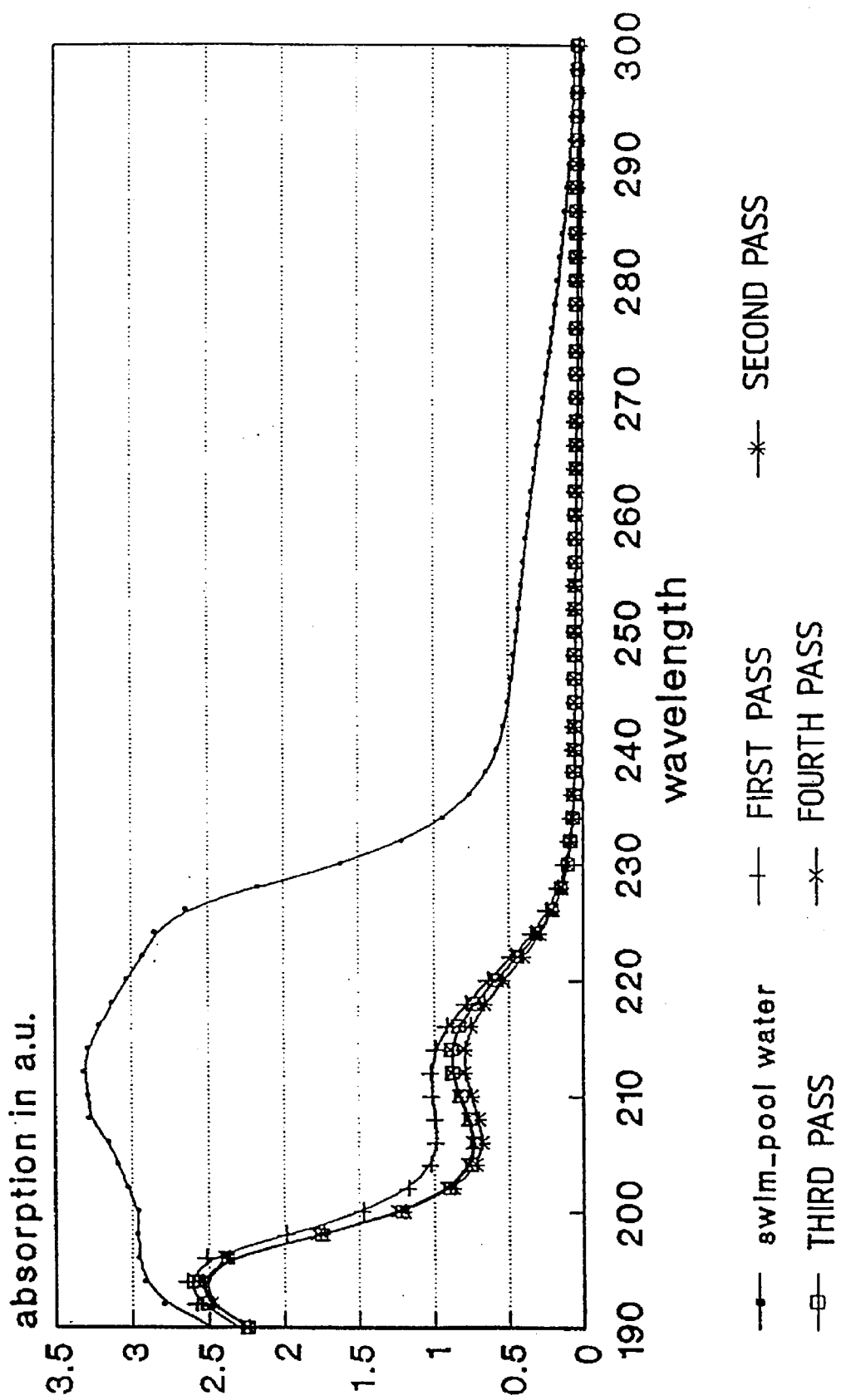
Figure 17:
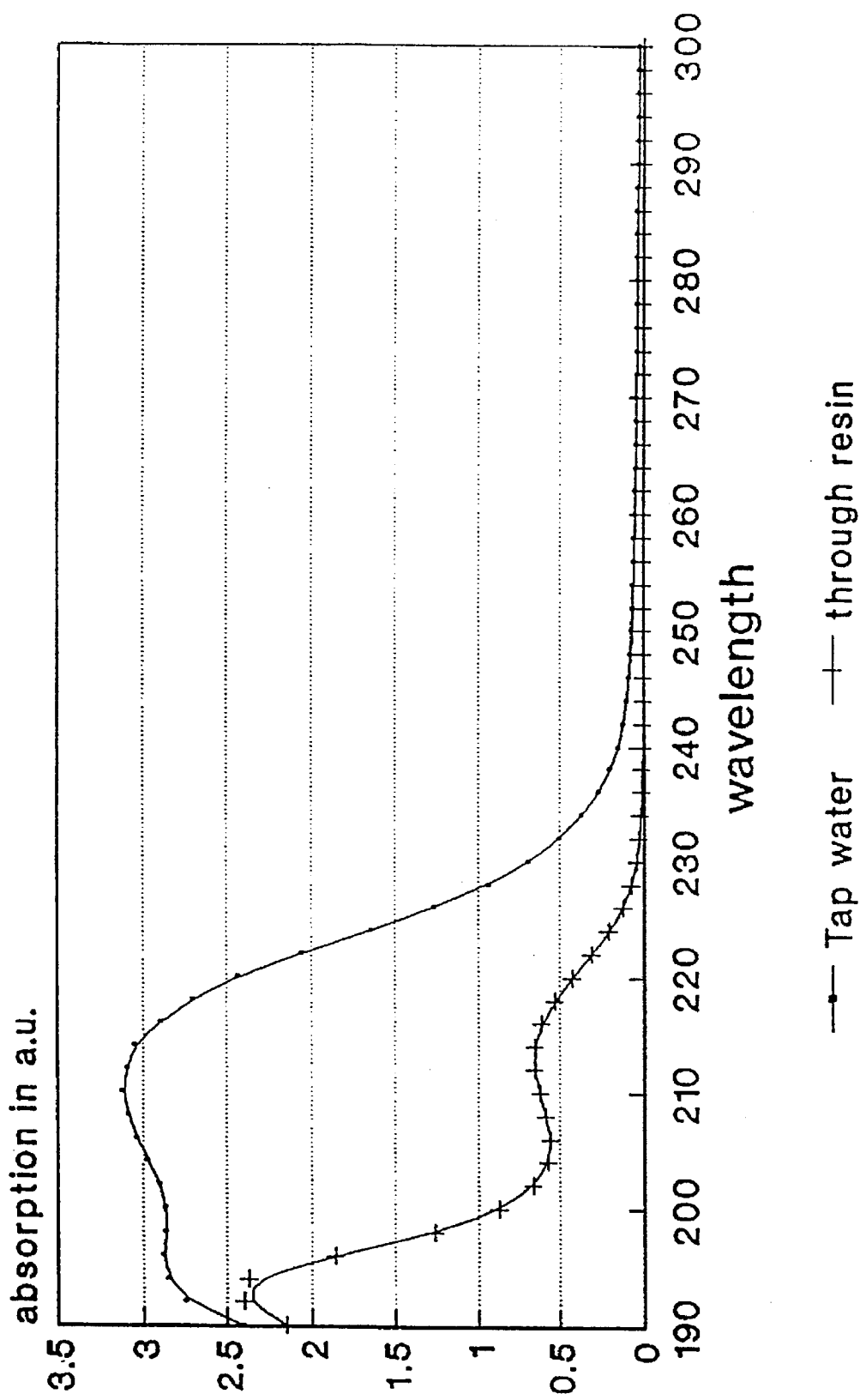

In the case of distilled water, practically all the nitrate which has been added prior to the filtering was removed as seen in FIG. 15. When swimming pool water was used (without adding nitrate since there is a large amount present) the response was not exactly the same. It revealed the presence of two peaks, the first one being at 195 nm while the second one was at 215 nm. The same sample was injected a second time into the same resin but it did not differ in response. In fact there was a fluctuating change around 6% as shown in FIG. 16. A similar result was obtained for tap water. FIG. 17 illustrates the scan through the ultra-violet region with a sample of tap water and the two peaks again appear after the sample was filtered using the resin.

Amberlite resin (HP555) was found to be very efficient in removing nitrate present in different source waters varying from distilled water to swimming pool water. Not only did it remove nitrate ions but chlorine as well. Hence it could be a very reliable source of background measurement of contaminated samples. This resin has been tested on different water samples. As It does not remove ammonia, a sample containing ammonia would be measured without the presence of a nitrate peak. The use of this resin provides for the background measurement of nitrate as well as organic matter.

Figure 18:
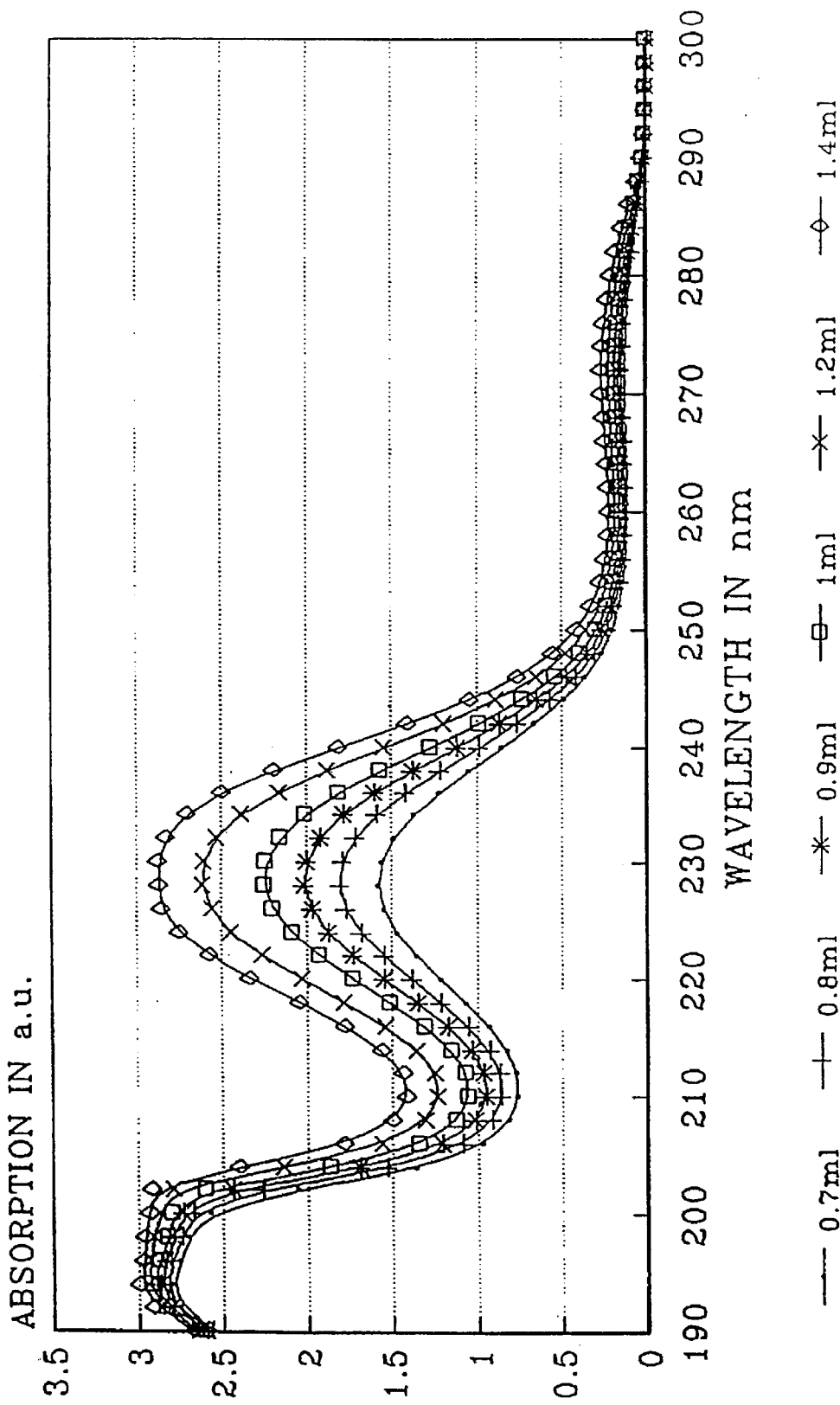
Figure 19:
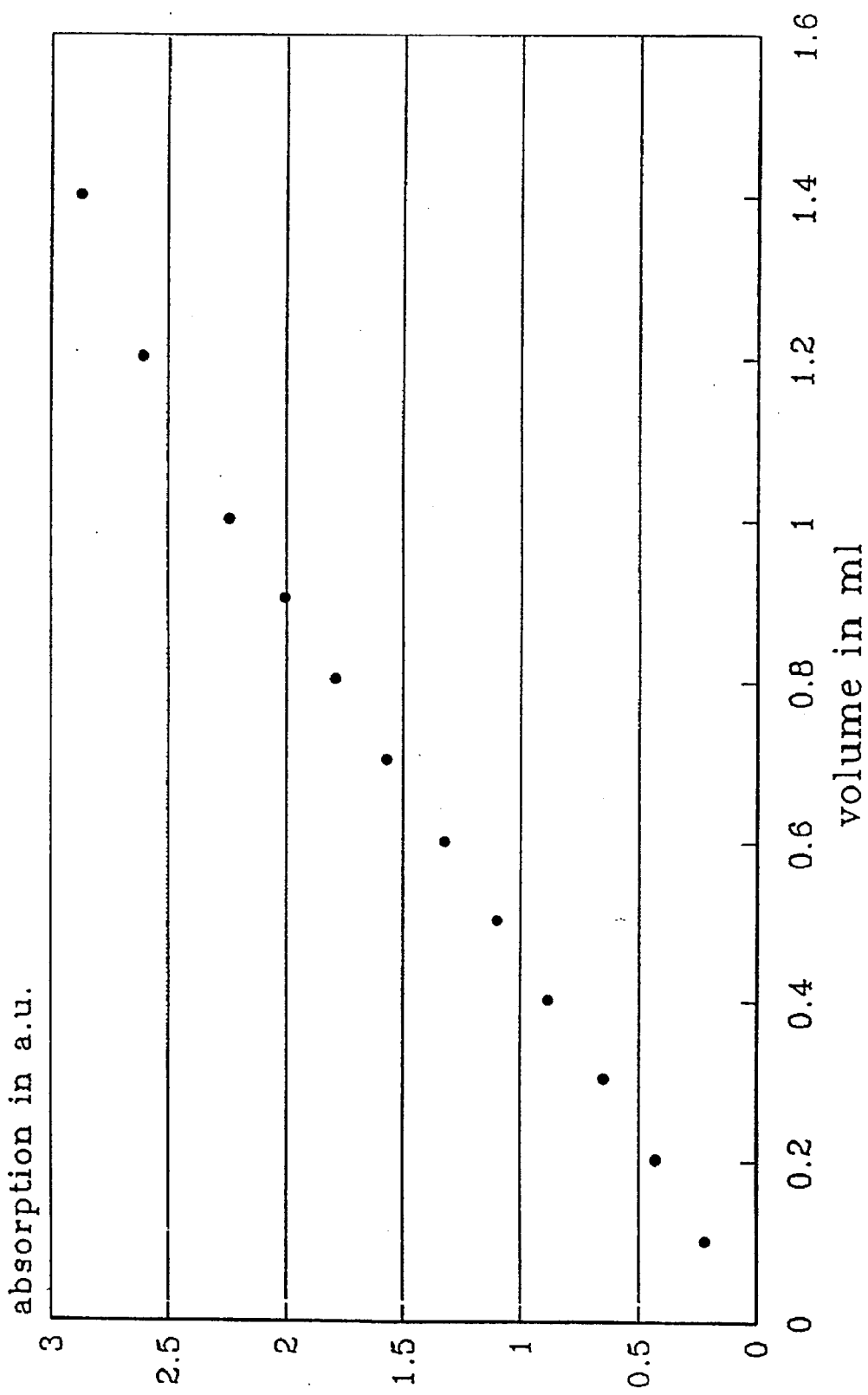

To simulate organic matter, benzoic acid was used. The scan of samples made from 2 g of benzoic acid dissolved in 100 ml of distilled water showed that there were two distinct peaks in the sub-300 nm region. The first peak which was situated at 230 nm was stronger than the one at 270 nm. Hence measurement at the first wavelength is more sensitive. However, this experiment was carried out in order to test the use of resin for organic matter removal. In general, organic matter has a large absorption band depending on the nature of the organic matter. Tests on samples of water showed a large baseline absorption rather than a peak as seen with benzoic acid. The nature of the organic carbon in these samples was not known. FIG. 18 gives the absorbance by different concentrations of benzoic acid versus wavelength and FIG. 19 the linear variation of optical density versus concentration.

In order to combine the measurement of ammonia and organic matter, a wavelength of 254 nm is used since monochloramine absorbs at 244 nm and organic matter has a broad absorption profile in the UV band. The choice of this wavelength which is the high intensity emission of the output of a low pressure mercury lamp, had been selected because of its practical use and associated reduced cost. In addition, the shape of the lamp for fiber compatibility and its high power emission are significant factors in the choice of this wavelength/lamp combination.

Nitrate ions, which absorb at 200 nm, require the use of an alternative source, namely a mercury-iodine low pressure lamp having a main spectral emission peak at 206 nm.

The measurement of the concentration of certain chemical species is based on the absorption of UV light by the molecules that form the species. The optical properties of these elements yield particular characteristics which in turn are used to differentiate them. For the measurement to be made conveniently, the sample is pumped into an optical cell where the interaction between light and the chemical species present in the sample occurs giving rise to an attenuation of the transmitted signal. Additionally, some signal processing is required to enhance the performance. The attenuation discussed above is related to the concentration of a particular species by using the Beer-Lambert law which states that the logarithm of the ratio of the detected to the emitted light is linearly proportional to the concentration of the particular element.

The relation is a function of the path length through which the light travels and the extinction coefficient of the chemical element, thus, $$Log(P/P_o) = -\epsilon LC \qquad (1)$$

where $P_0$ represents the initial power and P represents the exiting power of the light after interaction with the matter, $\epsilon$ is the extinction coefficient, L is the path length which C is the concentration of the absorbing species.

From equation (1) there is a requirement to determine the initial value of the light power in the absence of the species of interest, thus enabling a measurement to be made of the degree of light attenuation of the signal because of the presence of other absorbing species and instrumental sources of error.

Referencing is a technique used to provide a measure of any variation in light attenuation and instrumental instabilities which can occur in the overall measurement and which are not produced by the particular species of interest. The reference is provided by a method in which the species of interest is remove prior to the light interaction measurement by alternative methods such as reacting the sample with oxidizing or reducing agents as in the case of monitoring of chlorine concentration or by filtering the sample through an ion-exchange column. When monitoring nitrate ions, organic matter or ammonia, both of these methods have been used to provide a reference for each particular species. For the measurement of nitrate ion concentration, an ion exchange resin was utilized successfully. For organic matter a different ion-exchange resin was deployed and for ammonia concentration the reference was provided by measuring the intensity of the signal intensity prior to the addition of the chlorine to convert ammonia into monochloramine.

The multiparameter monitor comprises a liquid handling unit, an optical unit and a signal processing unit.

Figure 20:
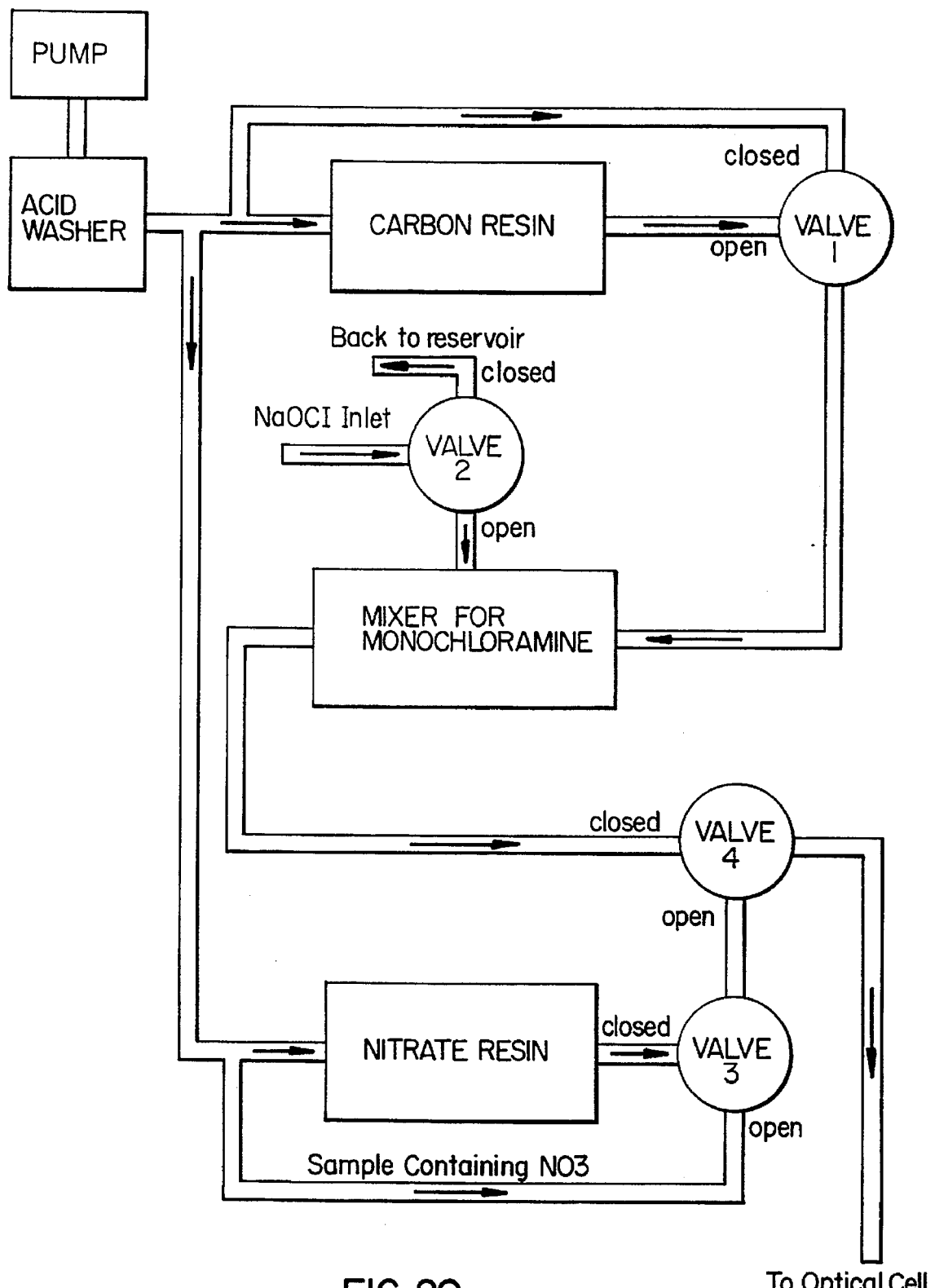
FIG. 20 shows a liquid handling unit.

The liquid handling unit is shown in FIG. 20. It comprises a pump, a set of electrical valves and ion exchange columns. A peristaltic pump driven at 100 rev/min using a 12 volt dc motor pumps a sample from a reservoir into the unit via a sample inlet port. The main advantage of using such a pump is the laminar flow it provides. In addition, there is complete isolation between the different flow channels and also between the mechanical part and the liquid part of the pump; this is important with corrosive fluids. The flow is then directed to a particular path subsequently by electrical valves activated from a central command circuit operating at 12v dc. Electronic circuitry generates appropriate signals to control the valves separately. The status of these signals and the combination of the valves' status for the measurement of one of the species is summarized in Table 1.

TABLE I

| Component | Valve 1 | Valve 2 | Valve 3 | Valve 4 |
|---|---|---|---|---|
| $NO_3$ ion | X | closed | O/C | open |
| $NH_3$ | closed | O/C | X | closed |
| organic matter | O/C | closed | X | closed |
| suspended matter | X | X | X | X |

A five channel micro-cassette head is used to pump the sample and reagents through the system. Two of these channels are used for the reagents and the remaining three are reserved for the sample. A collector tube is used to feed the flow from the three channels into the main feeder tube. The flow in this latter tube, increased by a factor of three, was found to be 180 ml/min and reduced the response time of the instrument considerably.

The sample tubing is made of silicone rubber and has a maximum internal diameter of 2.9 mm whereas the reagent tubing is made of Marprene and has an internal diameter of 0.5 mm. Hence the ratio of volume of reagent to sample is 1/100. This introduces an error of 1% in the concentration of the chemical species. The error is fixed because the ratio of the volumes of sample to reagent is constant as a result of the use of a peristaltic pump. However, this error is compensated during the calibration process by adding a constant multiplier factor to the output of the instrument. However, the use of liquid reagents applies only to the monitoring of ammonia since chlorine in the form of sodium hypochlorite solution is mixed with ammonia to produce monochloramine which absorbs at a wavelength of 254 nm. For measurement of nitrate ion and organic matter, no addition of reagents is required, but there is a longer delay time i.e. the time needed to fill the void space between the beads of the resin of the ion-exchange columns referred to earlier.

Figure 21:
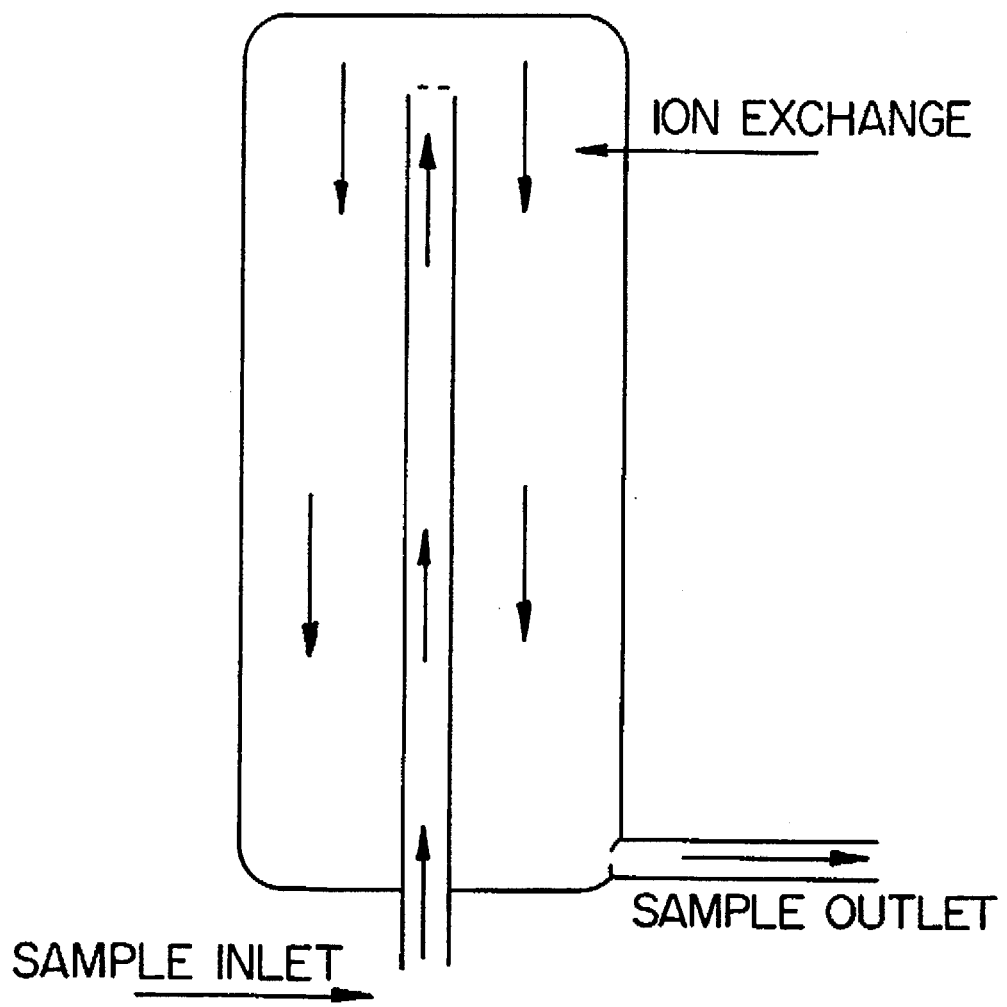
FIG. 21 shows an ion exchange column used in the apparatus of FIG. 1.

The ion exchange columns are made of glass. They are of cylindrical shape of 20 cm in length and 3 cm in diameter. A smaller column having a diameter of 2 mm is positioned inside the large column and is connected to the inlet of the ion exchange column. It has the function of guiding the sample so that it is evenly distributed over the resin which fills the volume between the large column and the inlet pipe. A small restriction is fitted to the outlet so that the beads cannot escape from the unit which is shown schematically in FIG. 21.

The sample flows to the optical cell directly where the measurement of the light attenuation is recorded and the data stored in a memory when valve 3 is open and valve 4 is open. Valve 3 is then closed and the sample is directed towards the nitrate resin to remove all the nitrate ion present. The sample is then sent to the optical cell to record the reference signal which represents the original intensity of the light source. A ratio of signal-to-reference is then obtained, recorded and displayed.

The pump is stopped every time a measurement is carried out to reduce the effects of fluctuations in sample flow on the data record.

Suspended matter can be measured using any wavelength in the ultra-violet, visible and infra-red regions of the spectrum. Hence the measurement of suspended matter can be carried out using an LED system rather than measurement in the ultra-violet because it is simpler and cheaper to build a fiber optic system for use in the infra-red region of the spectrum. The required sensitivity is provided by utilizing a powerful emitting LEDs and matching detectors.

A technique used for this measurement consists of demodulating the low frequency signal generated by the motion of the suspended matter where the sample flow is turbulent. The light is modulated electrically at a frequency of 0.5 to 1.0 MHz. Turbulent flow is generated by means of an obstacle put in the path of the sample. In the absence of any suspended matter, light scattered by the particles modulates the optical signal at a frequency proportional to the concentration of the suspended matter in the sample. Hence the root mean square of the decoupled low frequency signal provides a measure of the suspended matter present.

Because ammonia does not absorb at 254 nm a reference signal is obtained by measuring the attenuation of light at that wavelength and the ammonia is then converted into monochloramine which absorbs at 254 nm. To convert the ammonia to monochloramine, chlorine is added to the sample using valve 2 and a static mixer positioned before the last valve which valve 1 and 4 are closed. The ratio of the mixture is set by the diameter of the tubing and is 1 to 100.

Figure 22A:
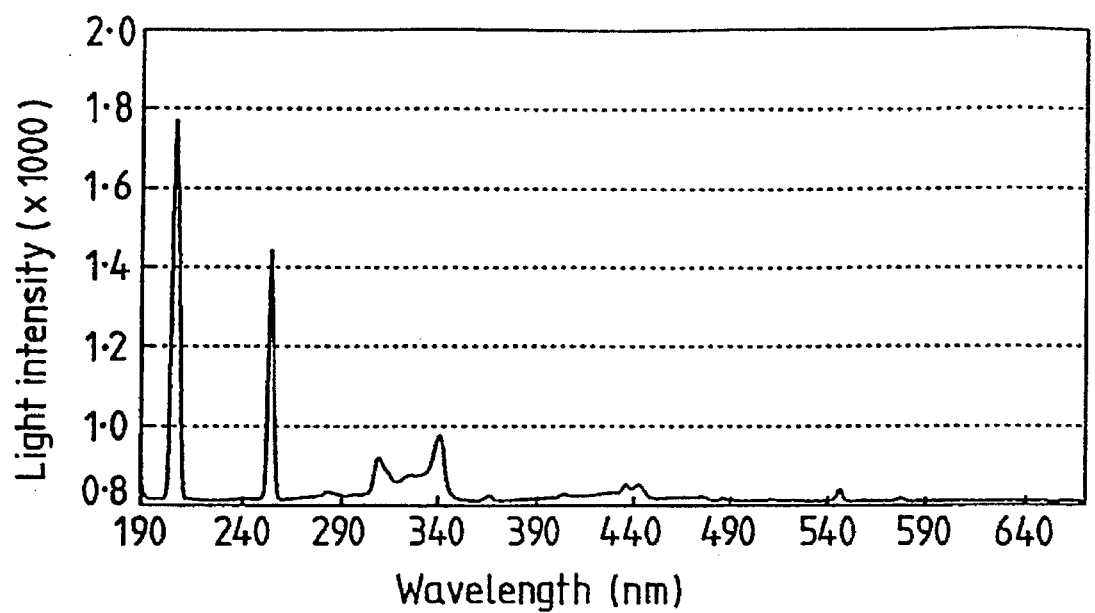
FIGS. 22a and b show emission spectra of UV lamps used in association with the apparatus of FIG. 1
Figure 22B:
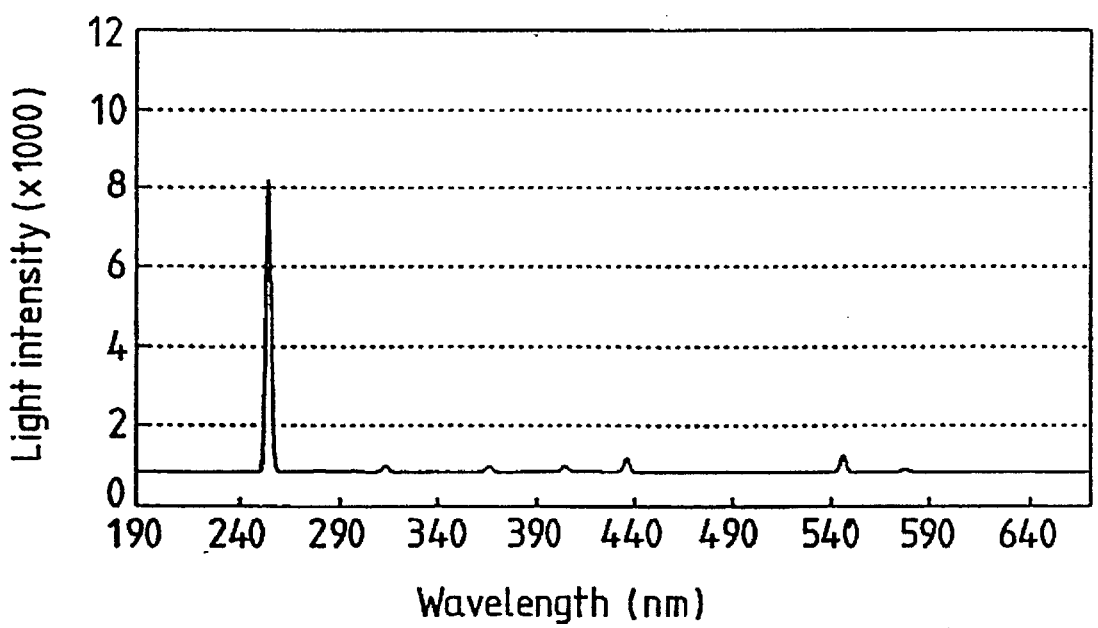

Ammonia, organic matter and suspended matter have an absorption peak around the main emission line (i.e. 254 nm) obtained from a low pressure mercury lamp, and nitrate ion, which absorbs at 200 nm, can be detected using a mercury-iodine low pressure discharge lamp which has an emission line at 206 nm. Its output spectrum is very pure i.e. only the emission lines of the vapor are present and not the additional lines that might be generated by the presence of other elements such as the material from which the electrodes are made. In this case the vapor is excited using a radio frequency (RF) signal, hence the higher operating frequency (200 KHz). The emission spectra of the UV lamps are shown in FIGS. 22a and 22b.

There are two automated options for guiding the light source to the optical cell. The first consists of using two separate fibers to guide the light from each source separately into the optical cell. With one large fiber carrying the light to the detector. The advantage in using this option resides in the fact that the two light sources are modulated with different frequencies i.e. 200 KHz and 30 KHz. Demodulating the two signals is then possible and made easier by either tuning the electronic filter in the control circuitry to the frequency of one source or the other. This can also be used by changing the frequency of the reference signal when a lock-in amplifier is used.

Figure 23:
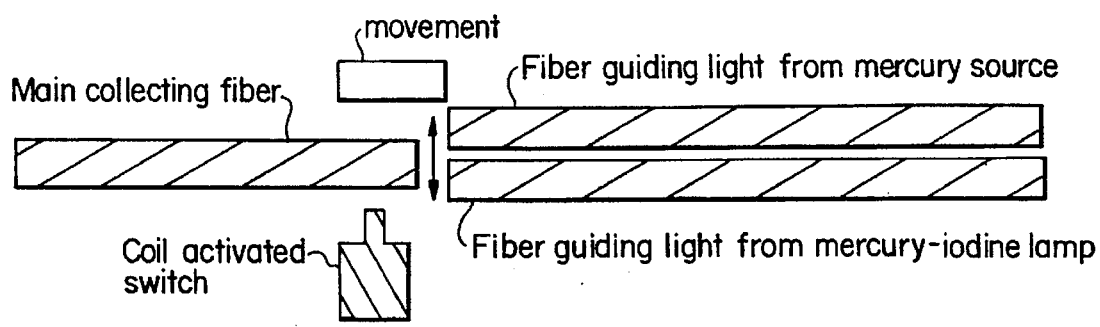
FIG. 23 shows an automatic fiber positioner.

The second option consists of using two short fibers to guide the light from each light source and then couple these two fibers into the main fiber using a fiber positioner. The latter consists of a coil actuated switch equipped with a piston which can push or pull the main fiber so that it is positioned in front of one of the two other optical fibers as shown in FIG. 23. The maximum movement of the main fiber is no more than 1 mm. However, the losses due to coupling are high and reduce the efficiency of light guidance in this system.

The fibers are made from quarts for maximum transmission of UV light. The diameter of the fibers is 1 mm and the overall size is 1.5 mm.

Figure 24:
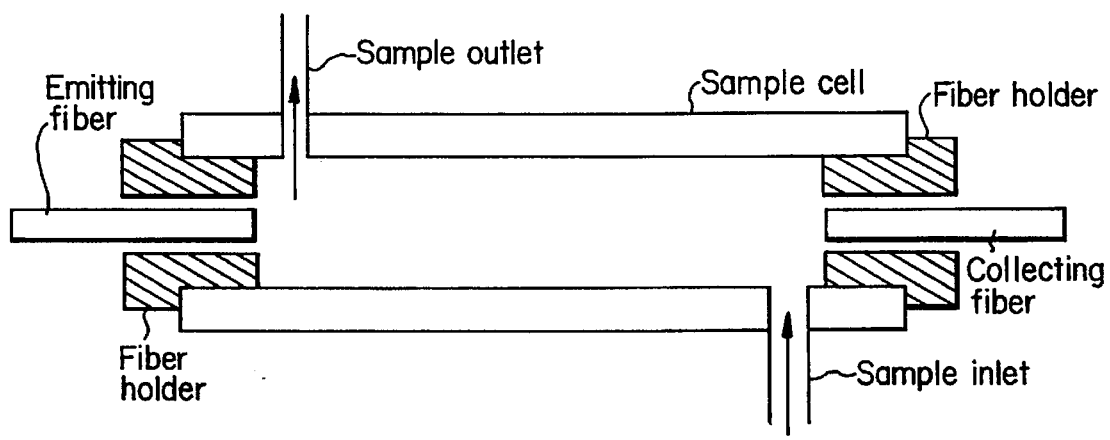
FIG. 24 is a side view of a sample cell.

The sample cell is a hollow cylinder made of Perspex, because it is transparent and easily machinable. At each end, a 1 mm fiber bundle is attached to enable light transmission through the cell. The inlet and outlet are positioned, diametrically opposite one another, one at each end of the cell as shown in FIG. 24. The length of the cell is fixed for the present experiments. However, for monitoring high concentrations of nitrate ion and because of its high absorptivity, a short path length only is needed e.g. smaller than 10 mm, whereas it is necessary to increase the path length when monitoring ammonia and organic matter since these have small extinction coefficients and hence a longer interaction length is required. (10 to 50 mm).

The optical cell is inclined at an angle of 30° so that air bubbles cannot be trapped inside it. With the exit of the sample being at the top end, any air bubbles present are flushed out of the cell.

Figure 25:
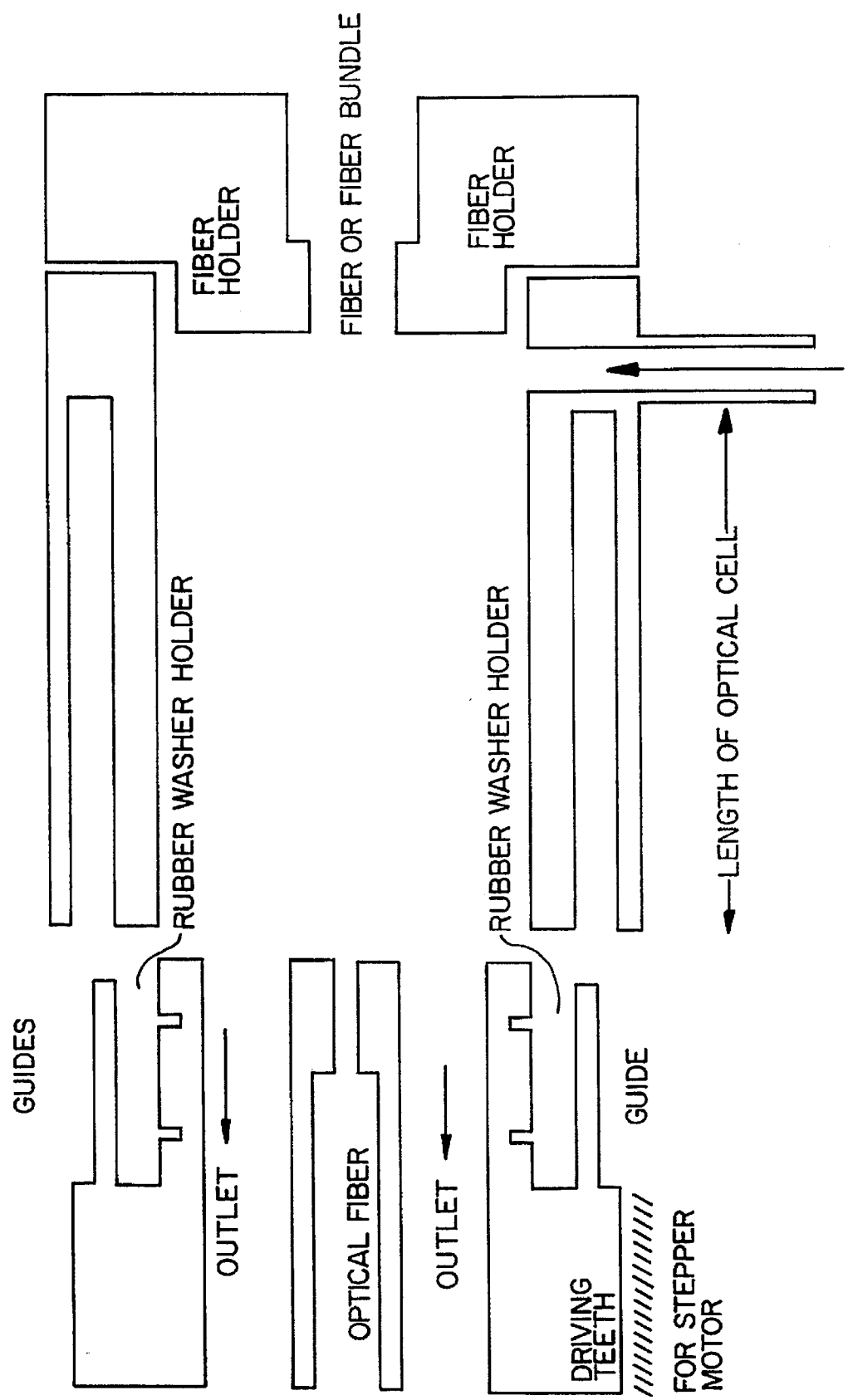
FIG. 25 shows an alternative sample cell.

A final design for the optical cell is shown schematically in FIG. 25. The major advantage of such a cell resides in the ability to vary the path length when required using a stepper motor. Thus the path length can be adjusted to predetermined value utilizing the timer and control unit or a microprocessor. The inlet and outlet are longitudinal and hence the cell should be mounted vertically to avoid trapping air bubbles inside the cell. The overall dimensions are such that the internal volume is kept to a minimum. The choice of materials for fabrication of such a cell has created a problem. The cell would have been very difficult to make from stainless steel because of machining difficulties at the dimensions required and would significantly increase the cost. It is therefore proposed to use machinable glass which possesses properties similar to stainless steel. Additionally it can be machined to the required shape and dimensions and then heated to acquire a strength similar to that of stainless steel.

The electronic system comprises the optical detector, the heterodyne modulator, the arithmetic and display section and the control circuitry.

Figure 26:
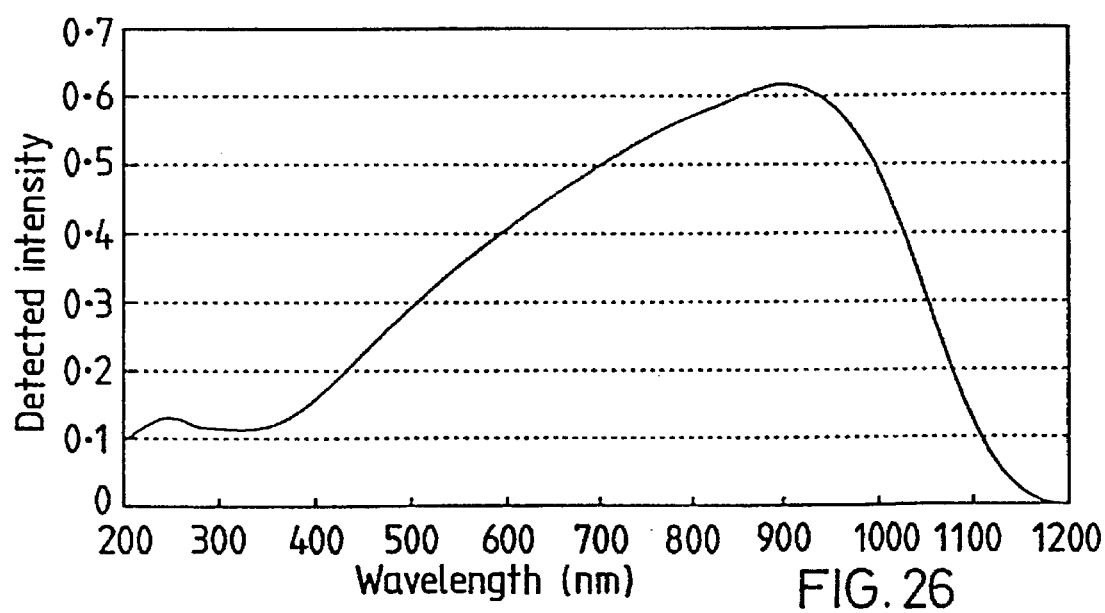
FIG. 26 shows the spectral response of a detector device.

The optical signal is converted into an electrical signal using a photodiode (PIN silicon type). Its characteristic has been improved in the UV region over other such devices and a quartz window allows the UV light to be transmitted through the semiconductor. The generated current is proportional to the light intensity and its spectral response is shown in FIG. 26. The ratio of sensitivity for near infra-red to UV is approximately 6. Hence there could be a need for an interference optical filter to reduce resulting errors. The sensitivity at 254 nm is 0.14 A/W, the detector has a noise figure of $10^{-14} W(Hz)^{-1/2}$. A transimpedance circuit converts the current signal into a voltage signal. It enhances the input impedance and reduces the loading effect on the diode. The output of this unit is proportional to the input current, as shown in the following formula:

$$V_{out} = f_s R_f \qquad (2)$$

where $R_f$ is the feedback resistor and $i_s$ is the current generated in the photodiode. The active component of this unit is a low bias current, low noise, large bandwidth operational amplifier. The maximum gain of this unit is limited by the gain bandwidth product (12 MHz) and its stability, restricting the feedback resistor value to 75K for a central frequency of 400 KHz. This limitation has the advantage of providing a means to eliminate the high frequency noise (higher than 500 KHz).

The implementation of the operation of a heterodyne detector, also known as a lock-in amplifier, consists of modulating the signal by a reference signal followed by a demodulation phase using a set of bandpass filters. This technique has the advantage of spreading the noise density over a larger band and thus reducing the noise spectrum per unit bandwidth. As a result the signal to noise ratio can be enhanced in comparison to that obtained with a normal detection technique.

This enhancement is then reflected in the sensitivity of the measurement especially for species which have a small extinction coefficient. The path length could be increased to increase sensitivity but that reduces the detected light intensity also and this then reduces the level of the detected signal. A higher gain amplifier is therefore required and this results In a higher noise level.

Figure 27:
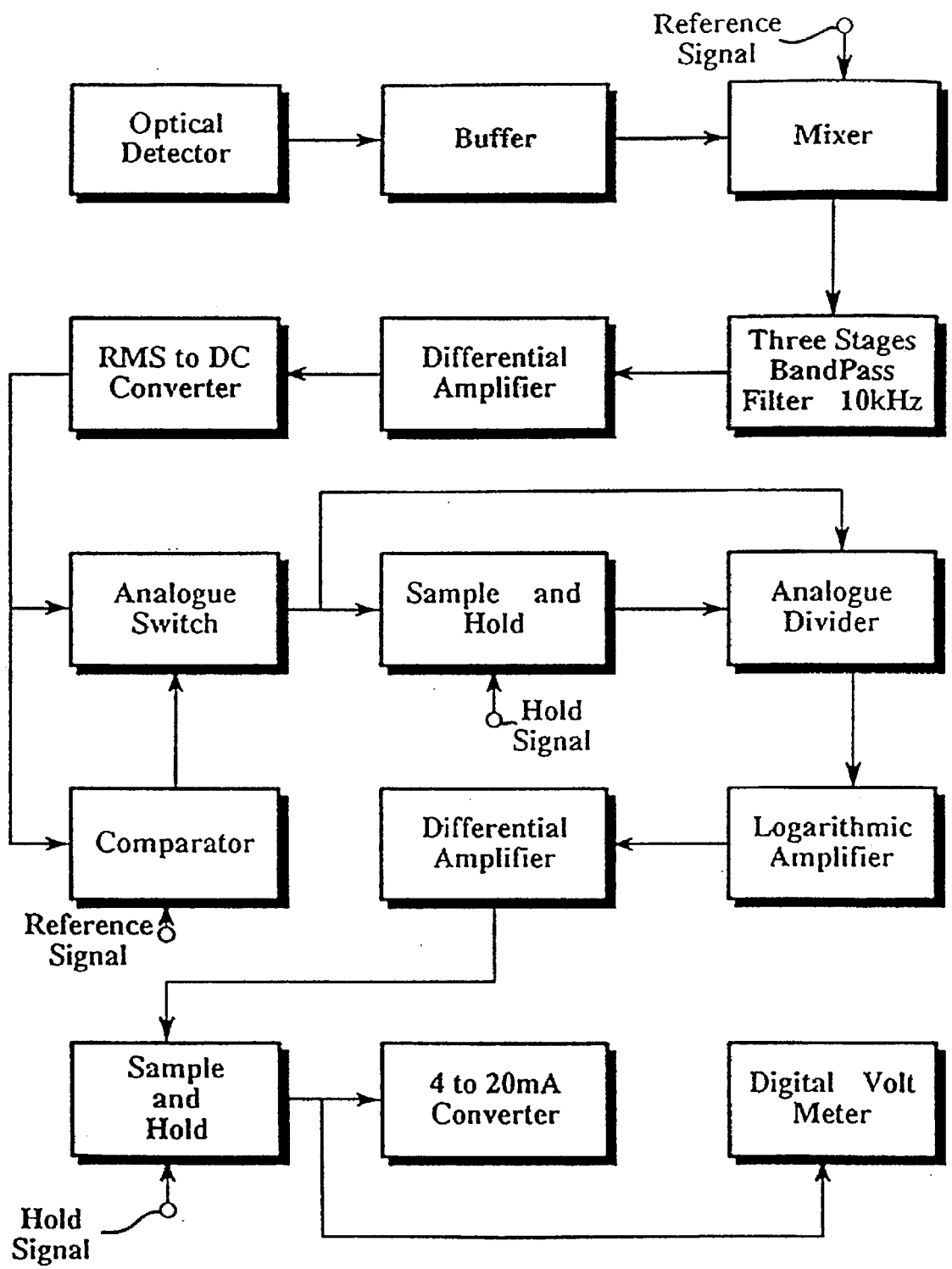
FIGS. 27 to 29 show the arrangement of various signal processing circuits.
Figure 28A:
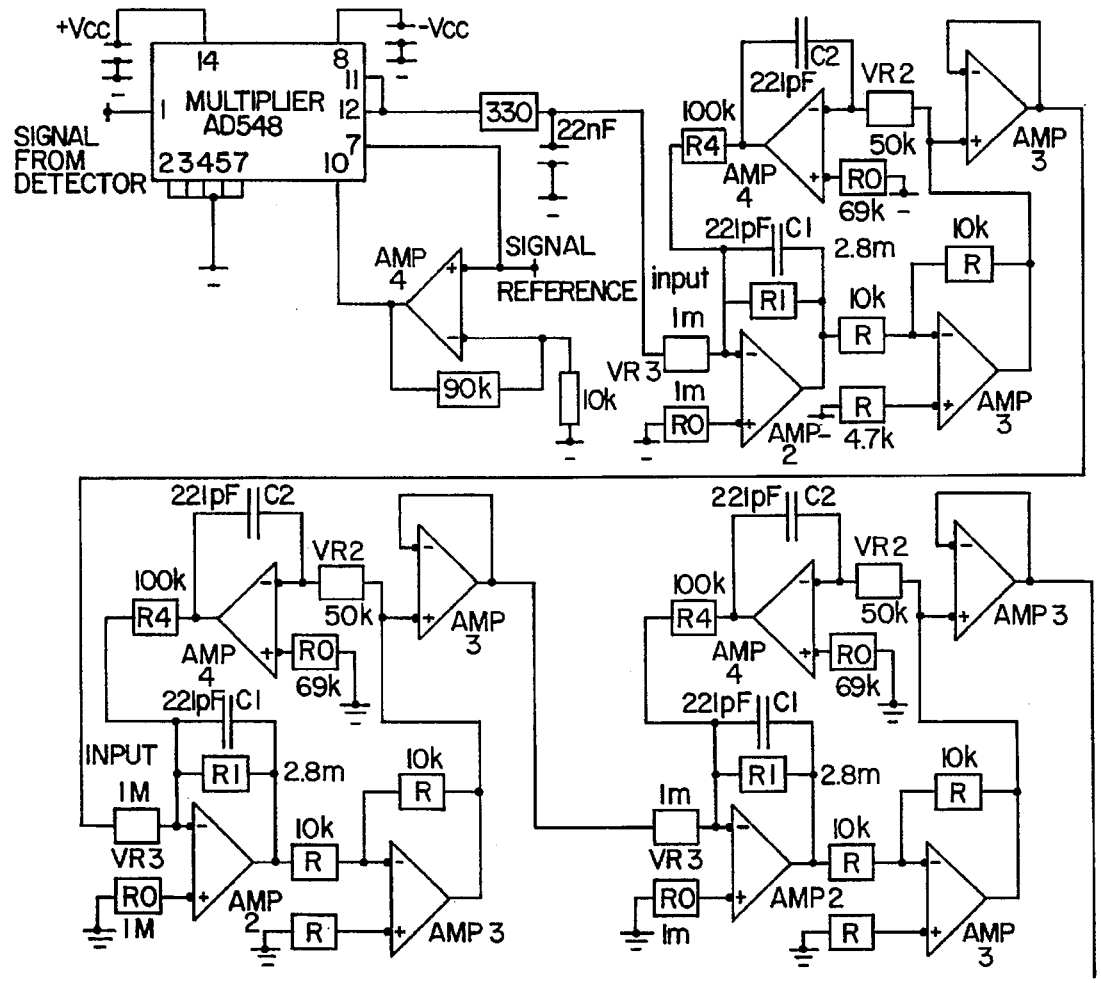
Figure 28B:
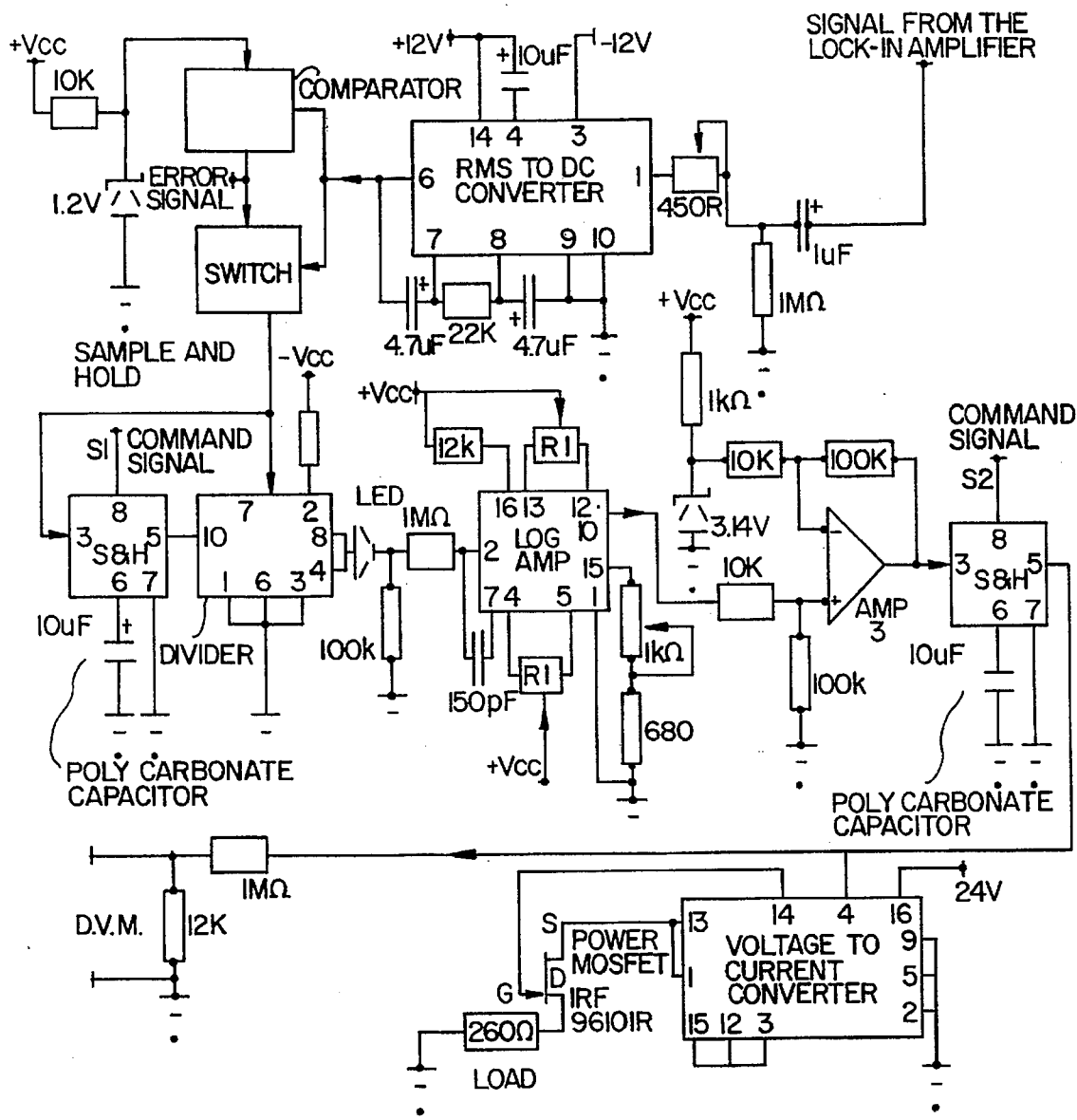

The detection is implemented using a four quadrant multiplier, a reference signal of a fixed amplitude of 500 mV and a frequency equal to the frequency of the detected signal to which 10 KHz has been added. The resulting signal consists of three components mixed together. One component represents the portion of the signal where the frequency is equal to the difference between the reference frequency and the detected frequency, the second portion being the carrier and the third portion contains the sum of the frequencies present. Only the portion containing the difference of frequencies is utilized in order to shift the working frequency to within the audio range i.e. 1 to 20 KHz. Hence a three stage bandpass filter is employed to reject the unwanted parts of the signal and to transmit only the desired side-band signal. The block diagram of the signal processing circuit is shown in FIG. 27 and the electronic circuit is shown in FIG. 28a and 28b.

A four quadrant multiplier was used as a modulator. The test was carried out on an existing mercury lamp and power supply which has not been modified. The detected signal had an amplitude of 200 mV and a frequency of 400 KHz. The reference signal was provided by a Marconi quartz controlled signal generator and provided a pure sinewave signal of 410 KHz at 500 mV. Three biquad bandpass filters were used to demodulate the output of the multiplier.

The signal processing unit consists of a combination of filters and amplifiers. Different noise sources, extrinsic and intrinsic to the system are superimposed on the main signal. The largest proportion of the noise signal (thermal and shot) originates mainly in the photodiode. The signal is fed to a biquad bandpass filter tunes at 10 KHz which eliminates undesirable frequencies such as the 50 Hz (electrical) and 100 Hz and dc (optical ambient light) as well as the 200 Hz emitted from the power supply of the lamp itself. The biquad filter is a tunable active bandpass filter, where the different gains, Q factor (Q) and central frequency are tuned separately. As a result of the limited bandwidth of the amplifiers, the maximum Q-factor achieved with his filter is 40. This particular type of operational amplifier has a bandwidth gain product of 6.4 MHz, a slew rate value of 34 µV/s a bias current of 32 pA and a noise figure at 10 KHz of 12 nV/Hz$^{1/2}$. The transfer function of such a filter is given by equation (3):

$$V_{out}/V_{in} = G/(1 + jR_1(C\omega - 1/C\omega V_{R2}R_4)) \quad (3)$$

where the different values of resistors and capacitors are shown in the electronic circuit $\omega$ is the operating frequency of the system.

The system resonates at a frequency given by equation 4 which is the mathematical solution of $$N(\omega) = 1 + jR_1(C\omega - 1/C\omega V_{R2}R_4) = 0 \quad (4)$$

$$W = (C_2 R_4 V_{R2})^{-1/2} \quad (5)$$

$$Q = (R_2/2)(R_3 R_4)^{-1/2} \quad (6)$$

To enhance the Q factor, three similar filters were cascaded giving a total Q factor of 120 and the bandpass of this filter block was then 600 Hz. The gain of the three bandpass filters was 140.

This setup has been tested on a signal provided by the residual chlorine monitor working at a frequency of 60 KHz. The only modification made was to change the reference frequency. The signal was taken from the output of the first stage of filtering, and improvement in the signal to noise ratio of 12 dB was achieved.

Figure 29:
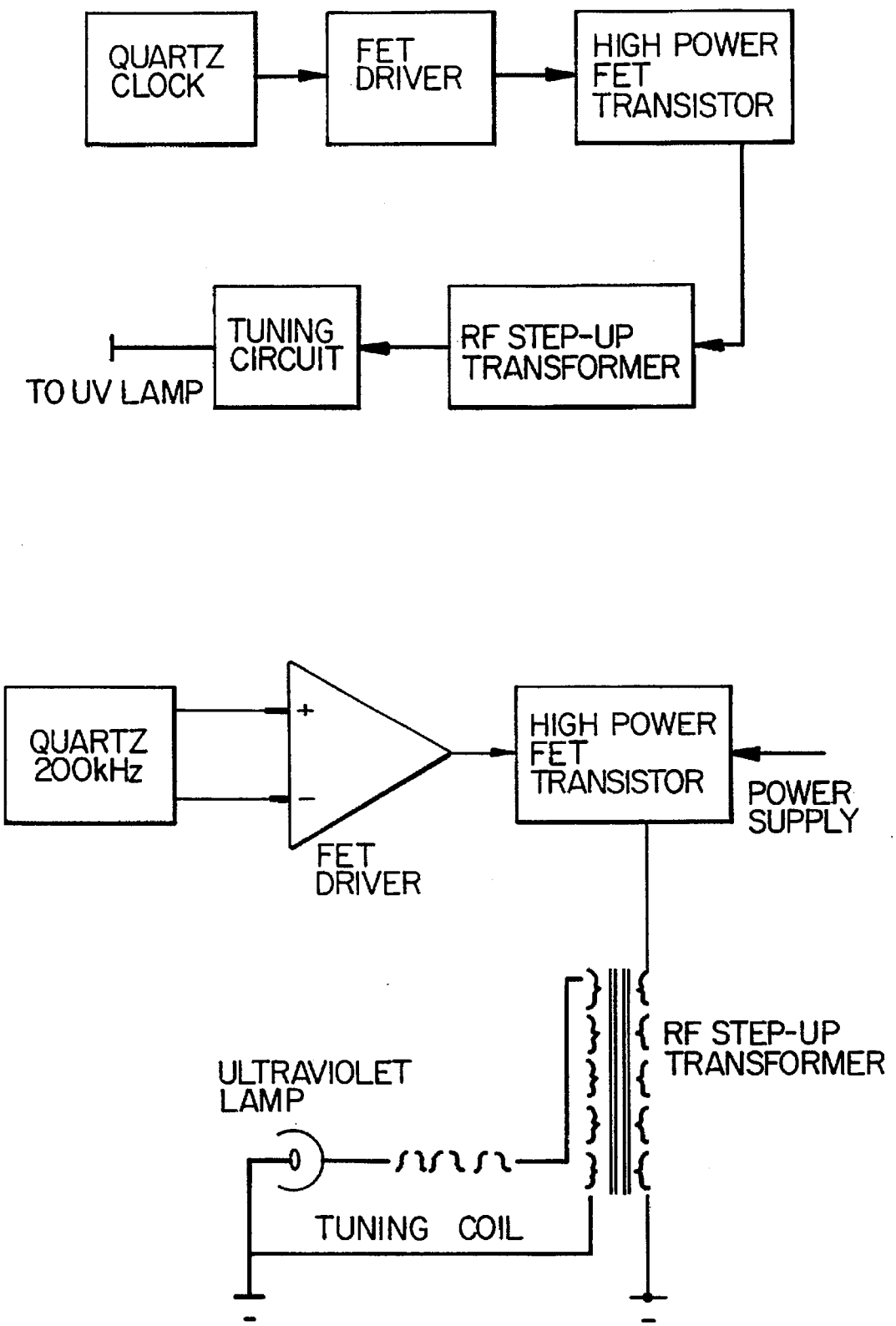

A quartz oscillator was incorporated as a fixed frequency reference standard and generated a digital signal of constant amplitude and a fixed frequency of 200 KHz. The frequency stability of the quarts is 200 ppm/°C. The signal is then applied to a power Field Effect Transistor (FET) which provides enough power to control the high power FET which supplies a square wave signal at 24 W (2A at 12V) to a high frequency high voltage transformer. The latter forms a tuned circuit with a couple of inductors and stray capacitance. In addition to stepping up the voltage to 3 KV, it filters the digital signal so that only the fundamental component of 200 KHz is transferred, all the higher harmonics are eliminated. This signal is then used to drive the lamp. The stability of the combination of the oscillator-lamp was tested over a full working day and a shift in its frequency output of only 5 Hz was found, i.e. a drift of 0.0025%. An additional reason for using such a system is to reduce the jitter which is present in the light output of UV lamps in particular, and most discharge lamps in general. This can be eliminated by taking the reference signal from the light source and mixing it with a fixed frequency using a suppressed carrier, single sideband modulation with an automatic gain controller. This way the reference which contains the information on the variation of the amplitude as it happens and can be subtracted from the detected signal. As a consequence the sensitivity of the measurement is increased further. This circuit is shown in FIG. 29.

The division computation utilizing analogue devices requires the availability of two signals at the same time when these signals are ac. However, the monitors perform the measurement of the reference and absorption signals sequentially so one of the two signals has to be stored in a sample and hold device until the other signal is available. This procedure is more easily implemented with dc signals hence the signal is converted to dc using an rms to dc converter. A second order filter is connected at the output to reduce the ripple present in the dc signal. The device chosen for this unit has a stable response and low drift characteristic. An external capacitor $C_{AV}$ is used to average the rectified ac signal and its value determines the magnitude of the ripple, which is considered to be an error and is superimposed on the dc signal. There is a compromise between the response time and the ripple rejection, since the smaller the capacitor (smaller settling time) the larger the ripple. The value of $C_{AV}$ is set to be 10 µF. The ripple rejection is increased by using a second order filter at the output of the device, increasing the response time while maintaining a good ripple rejection.

In order to measure the response of any element it is necessary to convert the logarithmic response of the Beer-Lambert law into a linear function. Thus in this way the calibration is easier to accomplish. When the reference for a particular signal is obtained, it is saved in a sample-and-hold circuit acting as a memory. The next cycle provides a measurement of the absorbed signal. The ratio of the two signals is then computed using an analogue divider. The signal is then amplified using a logarithmic amplifier and the relationship obtained, between detected signal and the concentration of the species present, is linear. A digital voltmeter (DVM) is used to measure this signal at its input and displays the result as a voltage. However, the DVM can be calibrated directly in terms of concentration. In parallel a 4-to-20 mA current port is supplied. The conversion is carried out using a current converter driving an FET through a load of 267Ω.

The third unit is for implementation of the arithmetic unit, i.e. the to ratio the absorption measurement signal to the reference.

The measurement of the reference and the absorption signal is carried out at two distinctive times during the cycle.

The reference signal is stored in a sample-and-hold device during the first half cycle. This latter is triggered to store the value of the signal at the last moment of the first half cycle while the pump is stopped in order to minimize any additional error due to turbulence within the cell. Large capacitors are used with the sample-and-hold circuit to retain the signal during the half cycle. Polycarbonate capacitors are used (10 µF for one minute hold time) since they have a very small drift coefficient. This signal is present at one input of the divider (denominator).

During the second half cycle the absorption signal is present at the numerator input since the sample-and-hold circuit is in hold mode. The divider now has the information (reference and absorption signals) at its inputs and therefore performs the division.

The divider used is an analogue device. The gain of this device (which is set to 6) is controlled by a resistor connected to the negative supply and can range from 3 to 10 depending on the value of the resistor used, as shown in equation (8), (R=9KΩ) so that the small variations resulting from the ratio can be amplified. The output of such a device is given by the following equation (7):

$$V_{out}=B(Z_2-Z_1)/(X_1-X_2) \quad (7)$$

here $Z_2-Z_1$ represents the differential numerator input, and $X_1-X_2$ is the differential denominator input and B is the gain factor and is given by the following relationship:

$$B=10R/(5.4+R) \quad (8)$$

where R is the resistance in KΩ. The divider can compute perfectly when its denominator is larger than one volt, otherwise it operates in a nonlinear region. Thus a circuit is incorporated to control the level of the denominator and is described subsequently.

Figure 30:
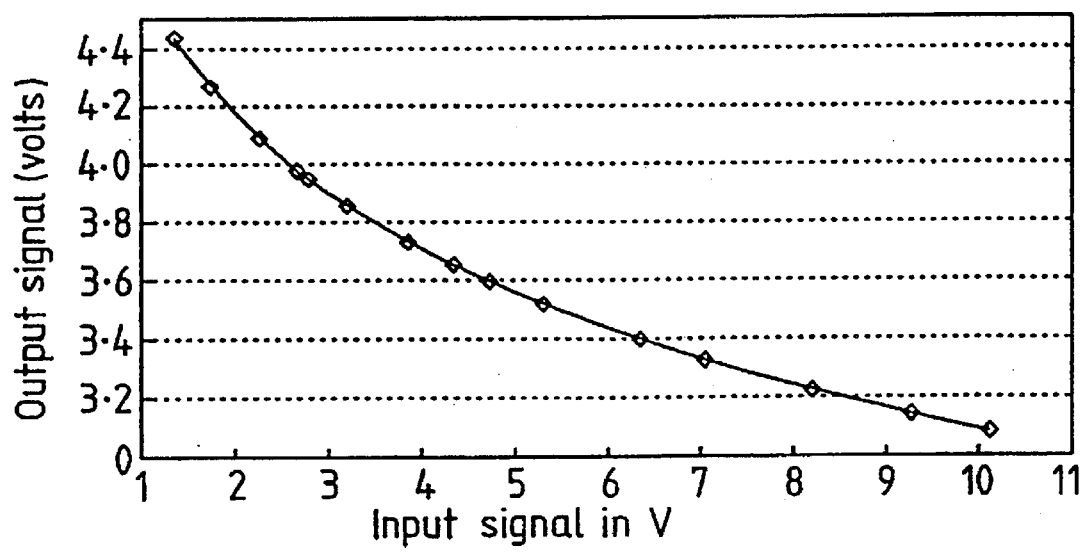
FIGS. 30 and 31 show the response of specific circuits.

The logarithmic amplifier transforms the input into a logarithmic output according to equation (10) and its graph is represented in FIG. 30.

$$Y=-1.57\log_{10}(V_{sig}/RI_{ref})+4.66 \quad (9)$$

where R=1MΩ and $I_{ref}$ is the reference current which is set to be 1 mA. The logarithmic amplifier compresses the dynamic signal making the range of output small (1.5V per decade change). The difference between the logarithmic output and a reference is amplified with a gain of 4.2. This signal is stored for one cycle. The output of the sample-and-hold device is routed to the 4 to 20 mA converter and to the digital voltmeter.

The digital voltmeter accepts a maximum dc signal of 199 mV and a bridge divider is incorporated to reduce the signal amplitude. This consists of a set of two resistors joined in series between the signal input and ground where the output is then taken from the second resistor. The DVM contains its own analogue to digital converter, reference voltage and display unit.

Figure 31:
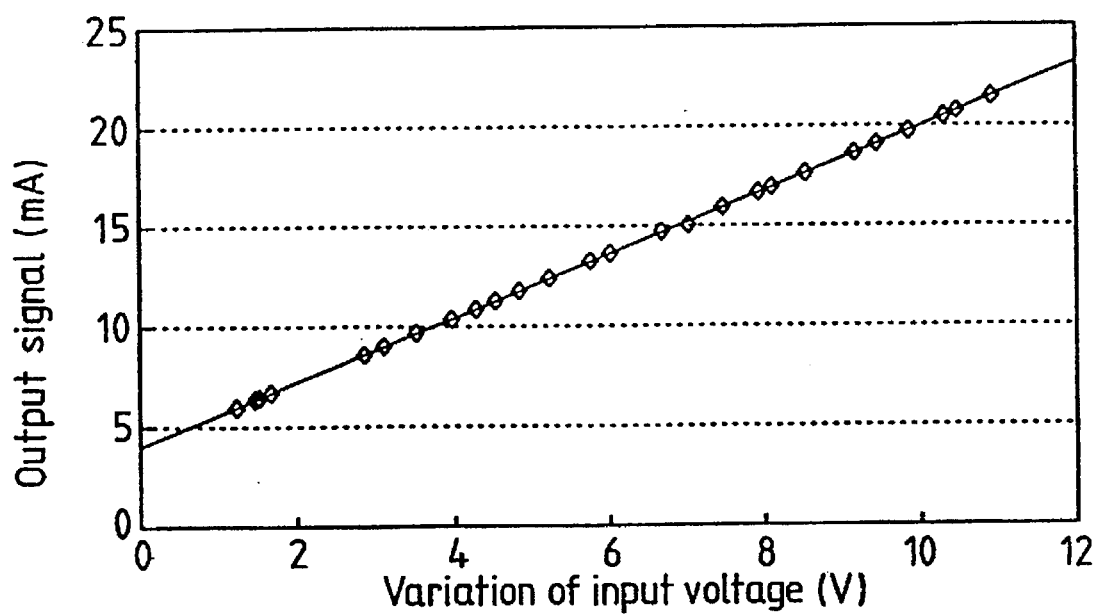
Figure 32A:
FIG. 32 shows the timing sequences from the different parts of a timer circuit.
Figure 32B:
Figure 32C:
Figure 32D:
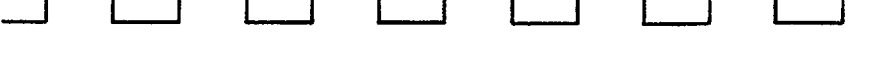
Figure 32E:
Figure 32F:
Figure 32G:
Figure 32H:
Figure 32I:
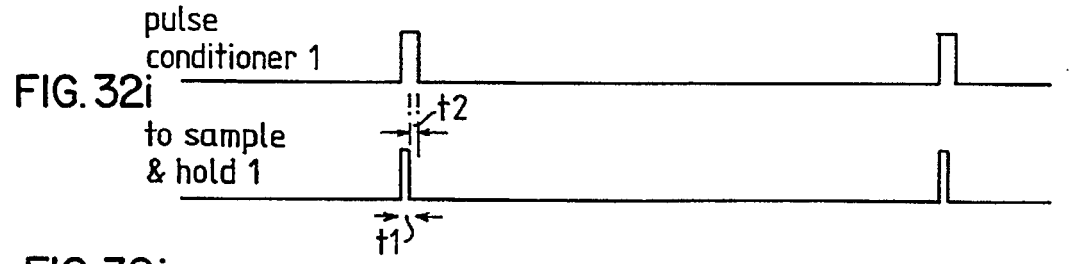
Figure 32J:
Figure 32K:

The instrument has a voltage to current converter for remote data acquisition, transforming the applied voltage into a proportional current. The component has been calibrated with a load of 267Ω as shown in FIG. 31. The signal is fed from the sample-and-hold memory through a buffer. The transfer function of this device is given by the following equation:

$$Y=1.6X+4.03 \quad (10)$$

where Y is in mA and X is in volts for a load of 267Ω.

The fourth unit consists of a combination of logic gates which generates a different type of control pulses to drive the sample-and-hold devices, the valve and the pump. The main clock signal is generated using a pulse generator working in an astable mode producing a 50% mark to space ration pulse of 0.5 Hz. This signal is used to activate the valve via a transistor switch. This valve requires a current of 130 mA in its holding mode. The same signal drives a dual binary counter from which all the sequences are generated using the same combinational logic. The pump is driven by a relay which is triggered by a transistor switch.

The timing for all the different parts of the monitor is generated from a simple timer. The measurement cycle is made up of two half cycles as follows:

1st half cycle: The sample is pumped through the resin column until the first volume that entered the column fills the optical cell. The pump is stopped for at least two seconds. A measurement of the light intensity reaching the detector is memorized in a sample-and-hold device. This is a reference signal.

2nd half cycle: the pump is activated and this time a valve is also activated so that the sample does not go through the column, but passes directly to the optical cell for the measurement of the attenuation of the light. At the end of this second cycle the ratio operation is computed and displayed on the DVM.

The appropriate signal for the pump, the sample-and-hold devices, the display and the error detection and correction are provided using logic gate circuitry.

An acid wash cycle is also provided to reduce the effect of fouling due to slow precipitation of cations in the water during long periods of operation. FIG. 32 shows the timing sequences from the different parts of the timer. This circuit also generates an appropriate timing sequence to take care of any problems occurring to provide appropriate alarms in the system. Problems could occur for a variety of reasons e.g. air bubbles in the optical cell or a decrease in the light intensity due to opaque samples. In this case the pump is activated until the source of error is eliminated and the system returned to the normal working state.

Since the signal must not drop below a value set at 1.2V e.g. as a result of bubbles in the light path or contamination of the sample, a switch is incorporated before the signal reaches the divider. A comparator compares the signal to the reference level of 1.2V and provides an input of +5V if the difference is positive, thus opening the switch. This pulse is used to reset the timer and the rest of the digital circuitry until the error is cleared. It also triggers a pulse generator to drive a warning red LED mounted on the front panel. In addition the pump is kept running until the timer sequence is re-established. The cycle always commences in the reference mode.

Figure 33:
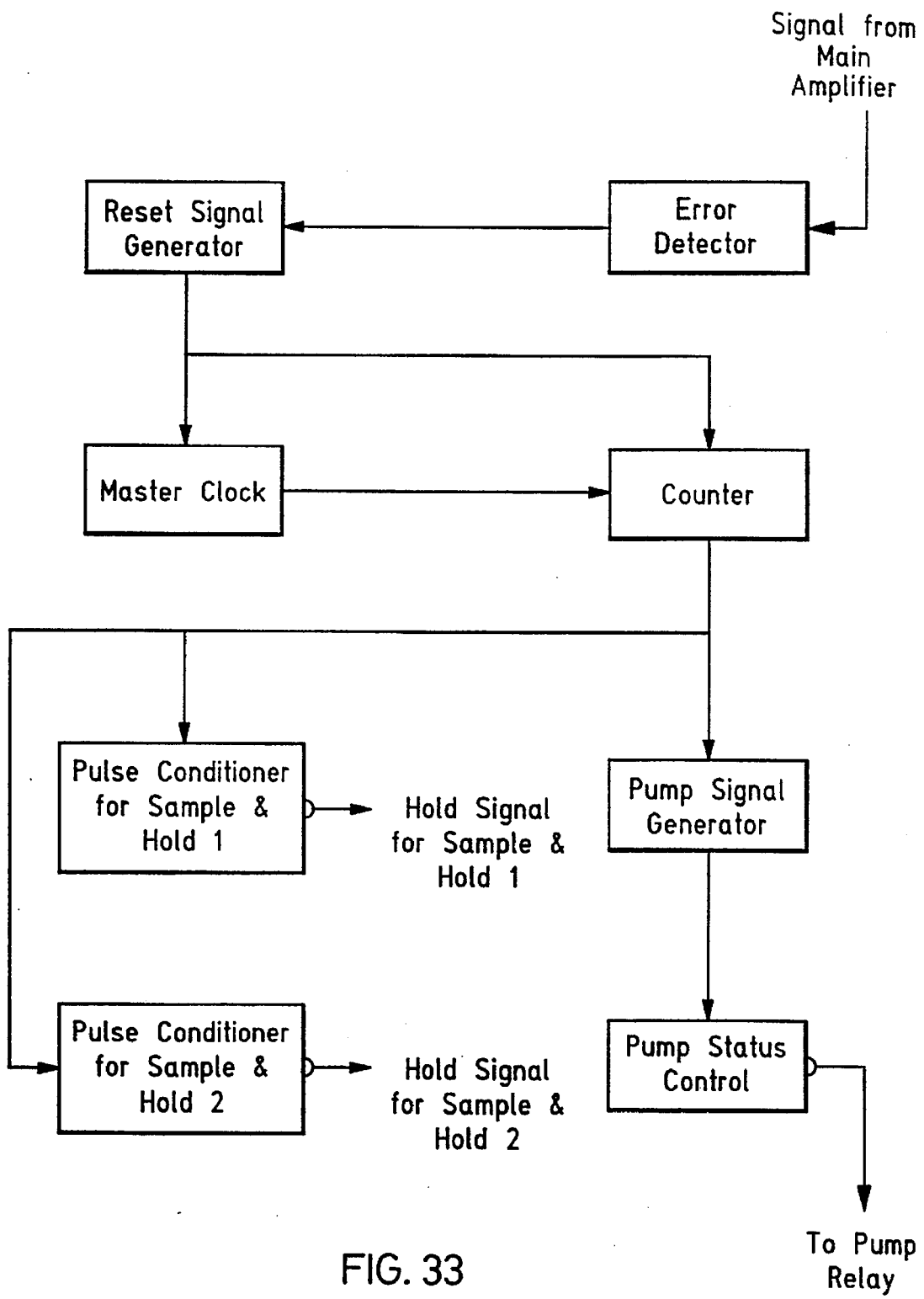
FIG. 33 is a block diagram of a timer and control unit.

To provide the sample-and-hold devices with command pulses to hold the signal, two flip-flops are used. Each flip-flop working as a multivibrator is connected differently so that the first flip-flop controls the triggering of the pulse while the second flip-flop controls the timing of the pulse. This is achieved with an RC network. The appropriate signals for the sample-and-hold device are generated from the pump and valve signals. The first multivibrator produces a pulse to control the divider sample-and-hold while the second controls the display sample-and-hold. These pulses are generated at the end of each half cycle when the pump stops. FIG. 33 represents the block diagram of the timer and control unit.

The static signal to noise ratio is calculated from equation (11):

$$S/N=20\log_{10}V_{signal}/V_{noise} \quad (11)$$

where $V_{signal}$ is usually the average value of the signal and $V_{noise}$ is the average value of noise. The static signal to noise ratio (S/N) is very important in order to assess the effect of noise on the measurement. The dynamic signal to noise ratio gives the actual ratio of the variation of the signal (between the two limits of transmission for the range of concentration of interest) and it also affects the ultimate sensitivity of the instrument since at this level the noise obscures the variation of the signal (i/e/ the magnitude of the noise is larger than the variation of the signal itself).

Due to the composition of mains tap water, cations can cause some disturbances to the liquid handling unit. Such problems can arise from precipitation of some cations e.g. calcium and magnesium, sometimes as crystals. These solids when present for a long time e.g. 2 to 3 hours can cause the silicone tubing to burst because of the action of the rollers on it. To eliminate this, an acid wash sequence is incorporated in the system. The latter is triggered every half an hour and dissolves any crystals that have formed in the tubing. It also removes any deposition of contaminant from the optical cell and fibers. When the prototype is in acid wash mode the measurement is suspended until it is reset to a normal working condition.

We claim:

1. Apparatus for measuring a concentration of a contaminant in a fluid, comprising;

a measuring chamber provided in a fluid path, a first source of optical radiation of a predetermined wavelength for directing said radiation through said measuring chamber, detector means to detect the radiation after passage through the measuring chamber, pump means provided in the fluid path to urge a test fluid from a fluid source to said measuring chamber, said test fluid being subject to containing said contaminant, fluid processing means provided in the fluid path to process said fluid to change an optical effect of said contaminant, acid washing means provided in the fluid path to inhibit the effect of precipitation of cations within the fluid path, bypass means provided in the fluid path to bypass said fluid processing means, and valve means provided in the fluid path alternately to direct said fluid to said fluid processing means and said bypass means.

2. Apparatus for measuring the concentration of a contaminant in a fluid according to claim 1, wherein said change is neutralization of said optical effect.

3. Apparatus for measuring the concentration of a contaminant in a fluid according to claim 1, wherein said change is introduction of said optical effect.

4. Apparatus for measuring the concentration of a contaminant in a fluid according to claim 1, further comprising a plurality of means for processing said fluid to change said optical effect in dependence on the presence of a corresponding plurality of contaminants in said fluid.

5. Apparatus for measuring the concentration of a contaminant in a fluid according to claim 1, further comprising a second source of optical radiation having different spectral characteristics from those of said first source of optical radiation and a second detector for radiation from said second source.

6. Apparatus for measuring the concentration of a contaminant in a fluid according to claim 2, wherein said fluid processing means incorporates resin means to absorb said contaminant.

7. Apparatus for measuring the concentration of a contaminant in a fluid according to any one of the preceding claims, wherein said detector means includes filter means for spreading detected optical noise over a larger bandwidth, thereby reducing a noise spectrum per unit bandwidth.

8. Apparatus for measuring the concentration of a contaminant in a fluid according claim 1, 2, 3, 4, 5 or 6, wherein said pump means includes a peristaltic pump.

* * * * *